United States Patent [19]

Bugaut et al.

[11] Patent Number: 5,026,401
[45] Date of Patent: Jun. 25, 1991

[54] DYEING COMPOSITIONS FOR KERATING FIBRES BASED ON NITROANILINES AND NITROANILINES FOR USE THEREIN

[75] Inventors: Andree Bugaut, Boulogne-Billancourt; Herve Borowiak, Aulnay-sous-Bois, both of France

[73] Assignee: L'Oreal, Paris, France

[21] Appl. No.: 406,818

[22] Filed: Sep. 13, 1989

Related U.S. Application Data

[63] Continuation of Ser. No. 783,070, Oct. 3, 1985, abandoned, which is a continuation of Ser. No. 425,857, Sep. 28, 1982, abandoned.

[30] Foreign Application Priority Data

Oct. 8, 1981 [LU] Luxembourg ............................ 83685
Nov. 4, 1981 [LU] Luxembourg ............................ 83730

[51] Int. Cl.$^5$ .................. A61K 7/13; C07C 211/49; C07C 215/20; C07C 217/44
[52] U.S. Cl. ......................................... 8/408; 8/409; 8/410; 8/414; 544/167; 546/232; 564/346; 564/367; 564/369
[58] Field of Search ................ 564/367, 369, 346; 8/408, 410, 414

[56] References Cited

U.S. PATENT DOCUMENTS

| | | | |
|---|---|---|---|
| 3,198,763 | 8/1965 | Peterli | 564/367 X |
| 3,446,568 | 5/1969 | Holzman et al. | 564/367 X |
| 3,697,215 | 10/1972 | Kalopissis et al. | 8/10.2 |
| 3,817,698 | 6/1974 | Kalopissis et al. | 564/367 X |
| 3,890,257 | 6/1975 | James | 564/369 X |
| 4,002,623 | 1/1977 | Kadin | 564/367 X |

FOREIGN PATENT DOCUMENTS

| | | |
|---|---|---|
| 1945451 | 4/1970 | Fed. Rep. of Germany . |
| 1520787 | 8/1978 | United Kingdom . |
| 1531605 | 11/1978 | United Kingdom . |

OTHER PUBLICATIONS

Foster et al., "Benziminazole Analogues of Biologically Active Indole Derivatives", *J. Chem. Soc.*, 1957, pp. 1671–1674.

Foster et al., "1-(2-Dialkylaminoethyl)-Methoxybenzimidazoles", *Recueil*, 82 (1963), pp. 583–586.

Primary Examiner—Glennon H. Hollrah
Assistant Examiner—Susan P. Treanor
Attorney, Agent, or Firm—Fleit, Jacobson, Cohn, Price, Holman & Stern

[57] ABSTRACT

There are described dyeing compositions for keratin fibres, and in particular for human hair, containing a dyestuff of the formula:

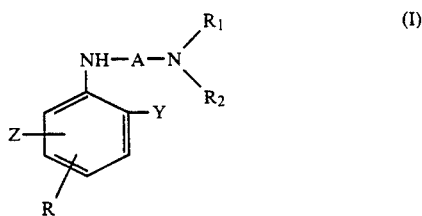

in which A denotes an alkylene group, an alkylene group substituted by one or more OH groups, or an alkylene group interrupted by a hetero-atom such as oxygen or by an —NH— group, $R_1$ and $R_2$, which are identical or different, denote hydrogen, alkyl, monohydroxyalkyl or polyhydroxyalkyl, or $R_1$ and $R_2$ can together form a heterocyclic ring chosen from among piperidino or morpholino groups, Y denotes alkoxy or $NO_2$, R denotes hydrogen or lower alkyl, and if Y denotes alkoxy, Z denotes $NO_2$ and is located in the para-position to the amine group, and if Y denotes $NO_2$, (a) Z denotes alkoxy or OH and is located in the para-position to the $NO_2$ group, or alternatively (b) Z denotes OH and is located in the para-position to the amine group, and also their cosmetically acceptable salts. Many of these dyestuff are novel.

18 Claims, No Drawings

DYEING COMPOSITIONS FOR KERATING FIBRES BASED ON NITROANILINES AND NITROANILINES FOR USE THEREIN

This application is a continuation of application Ser. No. 783,070, filed Oct. 3, 1985, now abandoned, which is a continuation of application Ser. No. 425,857, filed Sept. 28, 1982, abandoned.

The present invention relates to dyeing compositions for keratin fibres, and in particular for human hair, containing N-substituted nitroanilines as direct dyestuffs, to new nitroanilines used in these compositions and to a process for their preparation.

It is well known that, to give the hair a direct colouration, or a complementary sheen in the case of oxidation dyeing, it is possible to use nitro derivatives of the benzene series.

We have discovered that it is possible to obtain hair dyeings having a very good stability to adverse weather conditions and washing, and a good resistance to light, using a particular family of nitroanilines.

These compounds make it possible, in particular, to introduce yellow or orange-red into hair-dyeing formulations.

In addition to their noteworthy dyeing properties these dyestuffs have a good degree of harmlessness.

These dyestuffs can also be used in oxidation dyeing compositions for obtaining colourations with a rich sheen.

The present invention provides dyeing compositions for keratin fibres, in particular for human hair, which contain, in a medium suitable for dyeing, at least one dyestuff corresponding to the formula:

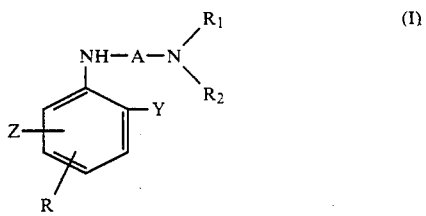

in which A denotes an alkylene group, an alkylene group substituted by one or more OH groups, or an alkylene group interrupted by a hetero-atom such as oxygen or an —NH— group, $R_1$ and $R_2$, which are identical or different, denote hydrogen, alkyl, monohydroxyalkyl or polyhydroxyalkyl, or $R_1$ and $R_2$ can together form a heterocyclic ring chosen from amongst piperidino or morpholino groups, Y denotes alkoxy or $NO_2$, R denotes hydrogen or lower alkyl (i.e. of 1 to 6, especially 1 to 4, carbon atoms) and if Y denotes alkoxy, Z denotes $NO_2$ and is located in the para-position to the amine group, and if Y denotes $NO_2$, (a) Z denotes alkoxy or OH and is located in the para-position to the $NO_2$ group, or alternatively (b) Z denotes OH and is located in the para-position to the amine group, and also their cosmetically acceptable salts.

In the above "alkylene" generally denotes a said group having 2 to 6 carbon atoms and preferably 2 to 4 carbon atoms. The alkyl and alkoxy groups preferably have 1 to 4 carbon atoms.

The compounds defined by the general formula (I) therefore correspond respectively to the following general formulae;

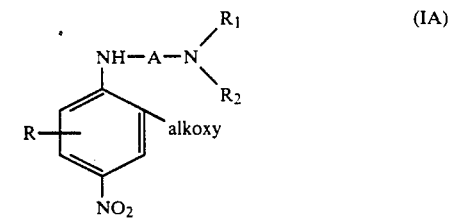

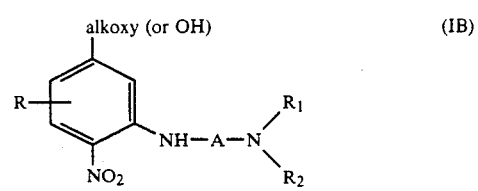

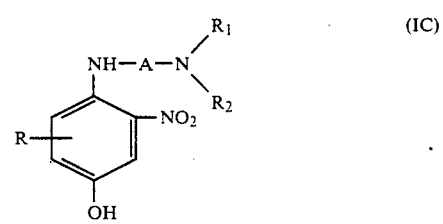

Amongst the above compounds, those which are particularly preferred are the ones in which A denotes ethylene, propylene or hydroxypropylene, R denotes methyl and Y or Z denotes methoxy.

Other preferred compounds are those of the formulae:

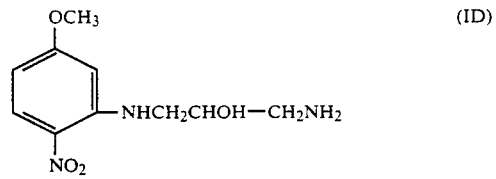

and
to

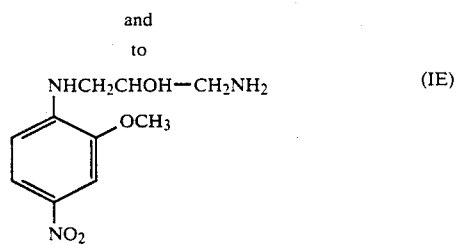

Amongst the compounds of the formula (I), a certain number of compounds are in themselves known and have been used as intermediates, for example in German Application 1,945,451, or referred to in the technical literature, such as in the article by Foster in JCS, 1,671-4 (1957) or in the article by Foster and Manson in Recueil, 82 (1963), pages 583-6.

The new compounds used according to the invention correspond to the following formula (II):

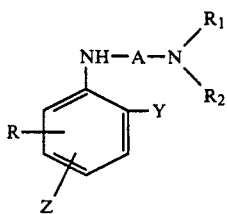

in which A denotes an alkylene group, an alkylene group substituted by one or more OH groups, or an alkylene group interrupted by a hetero-atom such as oxygen or by an —NH— group, $R_1$ and $R_2$, which are identical or different, denote hydrogen, alkyl, monohydroxyalkyl or polyhydroxyalkyl, or $R_1$ and $R_2$ can form a heterocyclic ring chosen from amongst piperidino or morpholino rings, R denotes hydrogen or lower alkyl, Y denotes alkoxy or $NO_2$, and

- if Y denotes alkoxy, Z is equal to $NO_2$ and is located in the para-position to the amine group, with the proviso that if Y denotes methoxy and A denotes the ethylene group, $R_1$ and $R_2$ do not simultaneously denote hydrogen, and
- if Y denotes $NO_2$: (a) Z denotes alkoxy or OH and is located in the para-position to $NO_2$, with the proviso that if Z denotes methoxy and A denotes the ethylene group, $R_1$ and $R_2$ cannot simultaneously denote hydrogen, methyl or ethyl, or (b) Z denotes OH and is located in the para-position to the amine group, in which case $R_1$ and $R_2$ have the meanings indicated above.

The preferred new compounds are those corresponding to the abovementioned formula (II) in which A denotes an alkylene group, an alkylene group substituted by one or more OH groups, or an alkylene group interrupted by a hetero-atom such as oxygen, $R_1$ and $R_2$, which are identical or different, denote hydrogen, alkyl, monohydroxyalkyl or polyhydroxyalkyl, or alternatively $R_1$ and $R_2$ can form a heterocyclic ring chosen from amongst piperidino or morpholino groups, R denotes hydrogen or lower alkyl, Y denotes alkoxy or $NO_2$, and

- if Y denotes $NO_2$, A denotes alkylene and Z denotes alkoxy and is located in the para-position to $NO_2$, $R_1$ and $R_2$ are different from hydrogen and alkyl, and
- if Y denotes $NO_2$ and Z denotes OH and is located in the para-position to $NO_2$, and also if Z denotes OH and is located in the para-position to the amine position, A, $R_1$ and $R_2$ have the meanings indicated above.

The following may be mentioned in particular: 3-[β-(N,N-diethyl)-aminoethylamino]-4-nitroanisole, 3-[γ-(N,N-diethyl)-aminopropylamino]-4-nitroanisole, 2-[β-(N,N-diethyl)-aminoethylamino]-5-nitroanisole, 3-β-aminoethylamino)-4-nitrophenol, 2-[β-(N,N-di-β'-hydroxyethyl)-aminoethylamino]-5-nitroanisole, 2-[γ-(N,N-dimethyl)-aminopropylamino]-5-nitroanisole, 3-nitro-4-[(N,N-dimethyl)-aminoethylamino]-phenol, 3-nitro-4-[(N,N-di-β-hydroxyethyl)-aminoethylamino]-phenol, 3-[β-(N,N-diethyl)-aminoethylamino]-4-nitro-6-methylanisole, 5-nitro-2-N-(3'-amino-2'-hydroxypropyl)-aminoanisole, 4-nitro-3-N-(3'-amino-2'-hydroxypropyl)-aminoanisole, 2-(β-hydroxy-γ-aminopropylamino)-5-nitroanisole and 3-(β-hydroxy-γ-aminopropylamino)-4-nitroanisole, this list not implying a limitation.

Amongst the compounds used according to the invention, those which are particularly preferred are the compounds of the formula (IB), which have excellent stability to adverse weather conditions and washing and a very good resistance to light and which make it possible to introduce yellow shades. Furthermore, the compounds of the formula (IC) are also very valuable insofar as they make it possible to introduce orange-red shades and insofar as they have a very good resistance to light, together with a very good resistance to adverse weather conditions and shampoos.

These compounds also exhibit the advantage of having a very good degree of harmlessness.

The compounds of the formula (IA) can be obtained by reacting the amines of the formula:

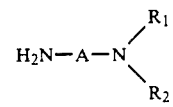

with the 3-alkoxy-4-methoxynitrobenzene or with a 3-alkoxy-4-chloronitrobenzene. They can also be obtained by condensing a halogen derivative of the formula:

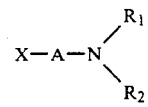

with a benzenesulphonamide or para-toluenesulphonamide, obtained by reacting benzenesulphonyl chloride or paratoluenesulphonyl chloride with the 2-amino-5-, nitro-1-alkoxybenzene, followed by acid hydrolysis of the substituted sulphonamide.

The compounds of the formula (IB) can be obtained by reacting an amine of the formula:

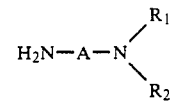

with 2-methoxy-4-alkoxynitrobenzene or with 2-chloro-4-alkoxynitrobenzene.

When $R_1$ and $R_2$ denote alkyl, the compounds of the formula (IB) can also be obtained by condensing a halogen derivative:

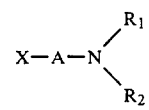

with a 2-arylsulphonylamino-4-alkoxynitrobenzenes, followed by acid hydrolysis of the substituted sulphonamides obtained.

The compounds of the formula (IC) can be obtained from the halogen derivatives of the general formula:

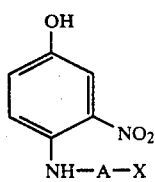

(III)

in which X denotes a halogen atom such as chlorine or bromine, either by reaction with an amine

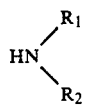

$R_1$ and $R_2$ having the meanings indicated above, or, if the aminoalkyl substituent of the aromatic amino group in the ortho-position to the $NO_2$ group contains a primary amine ($R_1$ and $R_2$ denote hydrogen), by reaction with potassium phthalimide, followed by treatment of the resulting substituted phthalimide with hydrazine (Gabriel's reaction).

The compounds of the formula (III) in which A denotes ethylene and X denotes bromine can easily be obtained by reacting hydrobromic acid with N-(2'-nitro-4'-hydroxyphenyl)-1,3-oxazolidin-2-one, which can itself be obtained by reacting dilute sodium hydroxide solution, at ambient temperature, with $\beta$-chloroethyl N-(2'-nitro-4'-hydroxyphenyl)-carbamate, described in the third step of Example 1 of French Patent 2,348,911, the disclosure of which is hereby incorporated by reference.

The compounds of the formulae (ID) and (IE) can be obtained, in particular, by reacting an amine of the formula $NH_2CH_2$—$CHOH$—$CH_2NH_2$ with a 3-alkoxy-4-methoxynitrobenzene or with a 2-methoxy-4-alkoxynitrobenzene.

The compositions according to the invention are characterised in that they contain at least one compound corresponding to the formula (I), in a cosmetically acceptable solvent medium, and can be used for the direct dyeing of keratin fibres or in the oxidation dyeing of these fibres, in which case the compounds of the formula (I) impart a complementary sheen to the base colouration obtained by oxidative development of oxidation dyestuff precursors.

These compositions suitably contain the compounds of formula (I) in an amount from 0.001 to 5% by weight, and preferably 0.01 to 3% by weight, relative to the total weight of the dyeing composition.

They can contain anionic, cationic, non-ionic or amphoteric surface-active agents or mixtures thereof, and preferably cationic and/or non-ionic surface-active agents. These surface-active products are suitably present in the compositions of the invention in an amount of 0.5 to 55% by weight, and preferably 2 to 40% by weight, relative to the total weight of the composition.

In these compositions, the vehicle generally consists of water, but it is possible to add organic solvents in order to solubilise compounds which would not be sufficiently soluble in water. Amongst these solvents there may be mentioned lower alkanols such as ethanol and isopropanol, polyols such as glycerol, glycols or glycol ethers such as 2-butoxyethanol, ethylene glycol, ethylene glycol monoethyl ether, propylene glycol, and diethylene glycol monoethyl ether and monomethyl ether, for example. These solvents are preferably present in an amount from 1 to 75% by weight, and in particular from 5 to 50% by weight, relative to the total weight of the composition.

The compositions can be thickened, preferably with, for example, sodium alginate, gum arabic, cellulose derivatives such as methylcellulose, hydroxyethylcellulose, hydroxypropylmethylcellulose and carboxymethylcellulose, and various polymers acting as thickeners, such as acrylic acid derivatives. It is also possible to use inorganic thickeners such as bentonite. These thickeners are preferably present in an amount from 0.5 to 10% by weight, and in particular from 0.5 to 3% by weight, relative to the total weight of the composition.

The compositions according to the invention can also contain various adjuvants normally used in hair-dyeing compositions, and, in particular, penetrating agents, sequestering agents, film-forming agents, buffers, perfumes, alkalising agents and acidifying agents.

These compositions can be presented in various forms such as a liquid, cream or gel or any other form suitable for dyeing the hair. They can also be packaged in aerosol flasks in the presence of a propellant.

The pH of these dyeing compositions is generally 3 to 11.5 and preferably 5 to 11.5. It can be adjusted to the desired value with an alkalising agent such as ammonia, sodium carbonate, potassium carbonate or ammonium carbonate, sodium hydroxide or potassium hydroxide, an alkanolamine such as mono-, di- or tri-ethanolamine, 2-amino-2-methylpropanol or 2-amino-2-methylpropane-1,3-diol, or an alkylamine such as ethylamine, diethylamine or triethylamine, or with an acidifying agent such as phosphoric, hydrochloric, tartaric, acetic, lactic or citric acid.

If the compositions are intended for use in a process of direct dyeing of the hair, they can contain, in addition to the compounds according to the invention, other direct dyestuffs such as azo dyestuffs, anthraquinone dyestuffs such as tetraaminoanthraquinone, aminoquinones, and nitro dyestuffs of the benzene series which are different from the compounds of the formula (I), and, more particularly, the following compounds: 3-nitro-4-amino-6-chloro-N-($\beta$-aminoethyl)-aniline, 3-nitro-4-N'-methylamino-N-($\beta$-aminoethyl)-aniline, 3-nitro-4-amino-N-($\beta$-hydroxyethyl)-aniline, 3-nitro-4-N-($\beta$-hydroxyethyl)-aminophenoxyethanol, 3-nitro-4-N'-($\beta$-aminoethyl)-amino-N,N-di-($\beta$-hydroxy-ethyl)-aniline, 3-nitro-4-N-($\beta$-hydroxyethyl)-amino-6-chloroaniline, 3-nitro-4-amino-6-methyl-N-($\beta$-hydroxyethyl)-aniline, N,N'-di-($\beta$-hydroxyethyl)-4-nitro-orthophenylenediamine, 2-nitro-N-($\beta$-aminoethyl)-aniline, 2-methyl-6-nitroaniline, 3-nitro-4-aminophenol, 3-nitro-4-N-($\beta$-hydroxyethyl)-aminophenol, 3-nitro-4-amino-6-methylphenol, 3-amino-4-nitrophenol, 2-amino-3-nitrophenol, 3-nitro-6-N-($\beta$-hydroxyethyl)-aminoanisole, 3-N-($\beta$,$\gamma$-dihydroxypropyl)-amino-4-nitroanisole, 3-N-methylamino-4-nitrophenoxyethanol, 3-N-methylamino-4-nitrophenyl-$\beta$,$\gamma$-dihydroxypropyl ether, N,N'-di-($\beta$-hydroxyethyl)-nitro-paraphenylenediamine and 3-nitro-4-N'-methylamino-N,N-di($\beta$-hydroxyethyl)-aniline. The concentrations of these direct dyestuffs other than the dyestuffs of the formula (I) is typically 0.001 to 5% by weight, relative to the total weight of the composition.

These compositions are applied to the keratin fibres for, say, 5 to 70 minutes and the fibres are then rinsed, optionally washed and rinsed again, and dried.

These compositions can also be used in the form of hair-setting lotions intended both for imparting a slight colouration to the hair and for improving the hold of the set. In this case, they are presented in the form of aqueous, alcoholic or aqueous-alcoholic solutions containing at least one cosmetic resin, and they are usually applied to damp hair which has been washed and rinsed beforehand, and the hair is optionally wound onto rollers and then dried.

The cosmetic resins used in the setting lotions can be, in particular, polyvinylpyrrolidone, crotonic acid/vinyl acetate or vinylpyrrolidone/ vinyl acetate copolymers, monoesters of maleic anhydride/butyl vinyl ether or maleic anhydride/ methyl vinyl ether copolymers, as well as any other cationic, anionic, non-ionic or amphoteric polymer normally used in this type of composition. These cosmetic resins are generally present in the compositions of the invention in an amount from 1 to 3% by weight, and preferably 1 to 2% by weight, based on the total weight of the composition.

If the compositions constitute oxidation dyes, the compounds of the formula (I) according to the invention are essentially used for the purposes of introducing a sheen into the final dyeing.

These compositions then contain oxidation dyestuff precursors in association with at least one nitro dyestuff of the formula (I).

They can contain, for example, para-phenylenediamines such as: para-phenylenediamine, para-toluylenediamine, 2,6-dimethyl-para-phenylenediamine, 2,6-dimethyl-3-methoxy-para-phenylenediamine, N-($\beta$-methoxyethyl)-para-phenylenediamine, 4-N,N-di-($\beta$-hydroxyethyl)-aminoaniline, 4-(N-ethyl-N-carbamylmethyl)-aminoaniline and also their salts.

They can also contain para-aminophenols, for example para-aminophenol, N-methyl-para-aminophenol, 2-chloro-4-aminophenol, 3-chloro-4-aminophenol, 2-methyl-4-aminophenol and their salts.

They can also contain heterocyclic derivatives, for example: 2,5-diaminopyridine and 7-aminobenzomorpholine.

The compositions according to the invention can contain couplers which are well known in the state of the art, in association with the oxidation dyestuff precursors.

Couplers which may be mentioned in particular are: meta-diphenols such as resorcinol and 2-methylresorcinol, meta-aminophenols such as: meta-aminophenol, 2-methyl-5-aminophenol, 2-methyl-5-N-($\beta$-hydroxyethyl)-aminophenol, 6-hydroxybenzomorpholine and their salts, meta-phenylenediamines such as: 2,4-diaminophenoxyethanol, 2,4-diaminophenyl $\beta$-hydroxypropyl ether, 6-aminobenzomorpholine, 2-N-(-hydroxyethyl)-amino-4-aminophenoxyethanol, 2,4-diaminopheny$\beta,\gamma$-dihydroxypropyl ether and their salts, and meta-acylaminophenols, meta-ureidophenols and meta-carbalkoxyaminophenols such as: 2-methyl-5-acetylaminophenol, 2-methyl-5-ureidophenol and 2-methyl-5-carbethoxyaminophenol.

Finally, the following may be mentioned as other couplers which can be used in the compositions of the invention: $\alpha$-naphthol, couplers possessing an active methylene group, such as diketone compounds, pyrazolones and heterocyclic couplers such as 2,4-diaminopyridine, and also their salts.

In addition to the oxidation dyestuff precursors, these compositions usually contain reducing agents and/or anti-oxidants such as sodium sulphite, thioglycolic acid, thiolactic acid, sodium bisulphite, ascorbic acid and hydroquinone. These agents are generally present in an amount of 0.05 to 1.5% by weight, relative to the total weight of the composition. The oxidation dyestuff precursors can be used in the compositions of the invention at a concentration of 0.001 to 5% by weight, and preferably 0.03 to 2% by weight, based on the total weight of the composition. The couplers can also be present in an amount of 0.001 to 5% by weight, and preferably 0.015 to 2% by weight, relative to the total weight of the composition. Their pH is preferably 7 to 11.5 and can be adjusted thereto with alkalising agents defined above.

The present invention also provides a process for dyeing keratin fibres, in particular human hair, using development by means of an oxidising agent, which comprises applying, to the hair, the dyeing composition comprising both a dyestuff according to the invention and one or more dyestuff precursors, and in developing the colouration with an oxidising agent which is either present in dyeing composition or is applied to the hair in a second step.

The oxidising agent is preferably chosen from amongst hydrogen peroxide, urea peroxide, and persalts. A hydrogen peroxide solution of 20 volumes strength is used in particular.

Once the composition has been applied to the keratin fibres with the oxidising agent, the keratin fibres are left for, say, 10 to 50 minutes, preferably 15 to 30 minutes, after which they are rinsed, optionally shampooed and rinsed again, and dried.

The Examples which follow further illustrate the present invention.

PREPARATION EXAMPLE 1

Preparation of 3-$\beta$-(N,N-diethylamino)-ethylamino-4-nitroanisole hydrochloride.

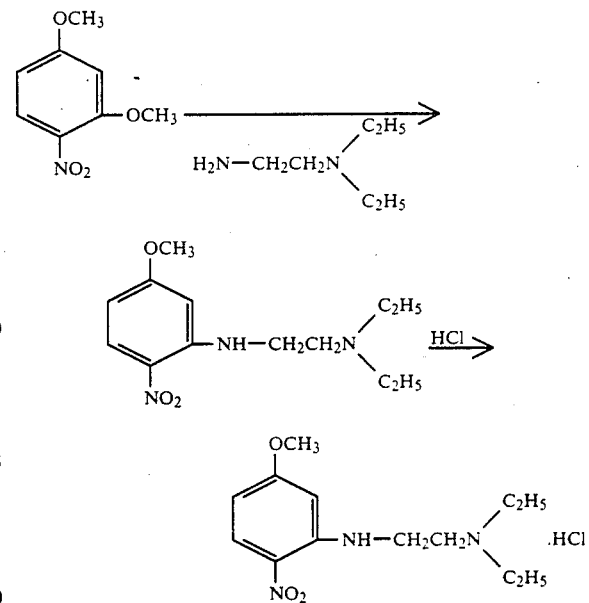

0.25 mol (46 g) of 2,4-dimethoxynitrobenzene is added to 140 ml of N,N-diethylethylenediamine and the reaction medium is then heated at 110° C. for 4 hours. After cooling, it is poured into 1.500 kg of iced water. The expected product is extracted with ethyl acetate. The ethyl acetate solution is dried with sodium sulphate and then cooled to 0° C. and 50 ml of ethanol saturated with hydrogen chloride are then added, with stirring. The 3-β-(N,N-diethylamino)-ethylamino-4-nitroanisole hydrochloride precipitates. It is filtered off, washed with ethanol and recrystallised from ethanol. After drying in vacuo, it melts at 157° C.

| Analysis | Calculated for $C_{13}H_{22}N_3O_3Cl$ | Found |
|---|---|---|
| C % | 51.40 | 51.37 |
| H % | 7.25 | 7.28 |
| N % | 13.84 | 13.91 |
| O % | 15.81 | 16.02 |
| Cl % | 11.70 | 11.83 |

PREPARATION EXAMPLE 2

Preparation of 3-γ-(N,N-dimethylamino)-propylamino-4-nitroanisole hydrochloride.

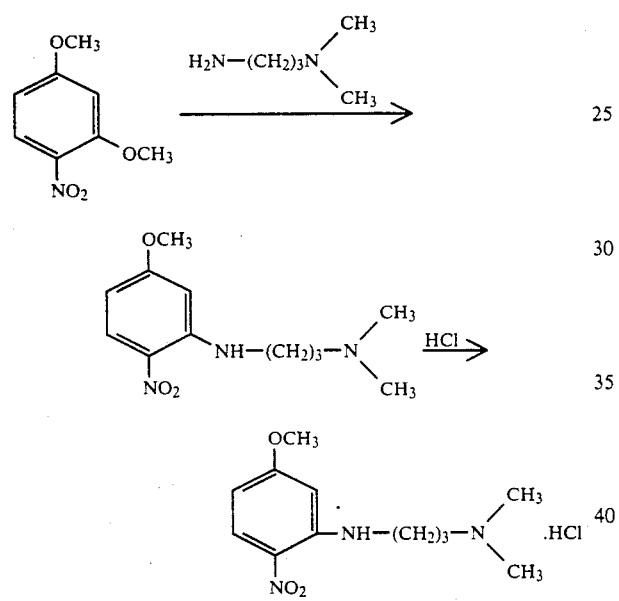

0.05 mol (9.15 g) of 2,4-dimethoxynitrobenzene is added to 30 ml of N,N-dimethylpropylenediamine and the reaction mixture is then heated at 110° C. for 4 hours.

After cooling, it is poured into 300 g of iced water and the oil which has precipitated is extracted with ethyl acetate. After drying over sodium sulphate, the ethyl acetate phase, cooled to 0° C., is treated with 10 ml of ethanol saturated with hydrogen chloride.

The 3-γ-(N,N-dimethylamino)-propylamino-4-nitroanisole hydrochloride precipitates. It is filtered off, washed with ethanol and recrystallised from ethanol. After drying in vacuo, it melts with decomposition at 204° C.

| Analysis | Calculated for $C_{12}H_{20}N_3O_3Cl$ | Found |
|---|---|---|
| C % | 49.74 | 49.77 |
| H % | 6.91 | 7.03 |
| N % | 14.51 | 14.36 |
| O % | 16.58 | 16.76 |
| Cl % | 12.26 | 12.45 |

PREPARATION EXAMPLE 3

Preparation of 2-β-(N,N-diethylamino)-ethylamino-5-nitroanisole hydrochloride.

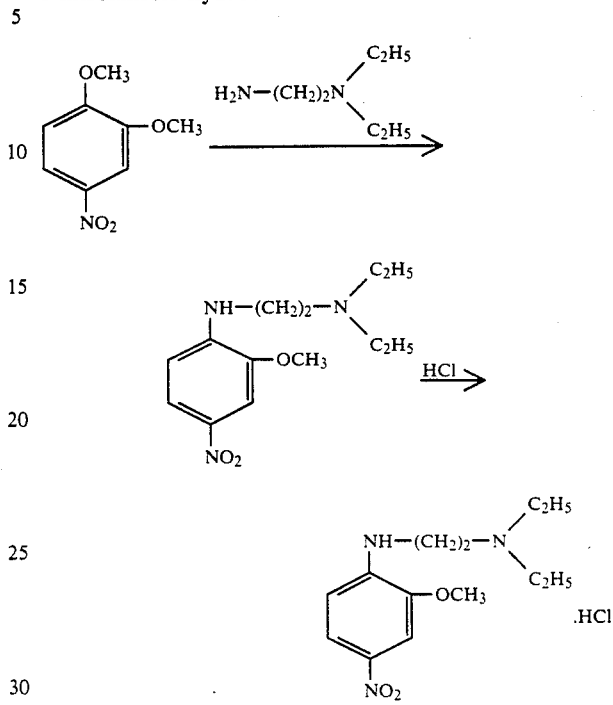

0.05 mol (9.15 g) of 3,4-dimethoxynitrobenzene is introduced into 30 ml of N,N-diethylethylenediamine and the solution is heated at 110° C. for 15 hours. The cooled reaction mixture is then poured into 300 g of iced water. The expected product, as the free base, precipitates in the form of an oil, which is extracted with ethyl acetate. The ethyl acetate is driven off in vacuo. The residual oil is dissolved in 15 ml of absolute ethanol. After the addition of 10 ml of absolute ethanol saturated with hydrogen chloride, a precipitate of 2-β-(N,N-diethyl-amino)-ethylamino-5-nitroanisole hydrochloride is obtained, which, after recrystallisation from ethanol at 85° and drying in vacuo at 60° C., melts with decomposition at 230° C.

| Analysis | Calculated for $C_{13}H_{22}N_3O_3Cl$ | Found |
|---|---|---|
| C % | 51.40 | 51.41 |
| H % | 7.25 | 7.21 |
| N % | 13.84 | 13.90 |
| O % | 15.81 | 15.77 |
| Cl % | 11.70 | 11.68 |

PREPARATION EXAMPLE 4

Preparation of 3-β-aminoethylamino-4-nitrophenol hydrochloride.

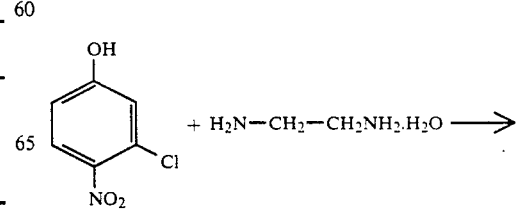

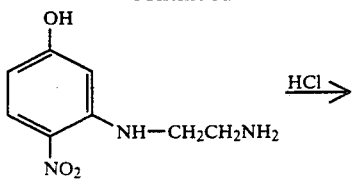

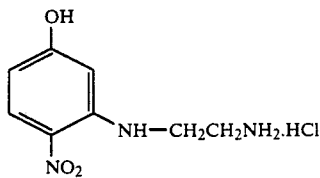

0.432 mol (75 g) of 3-chloro-4-nitrophenol is introduced into 282 ml of ethylenediamine and the reaction medium is then heated in a boiling water-bath for 13 hours. The cooled solution is then poured into 2.6 liters of iced water to which 1.09 liters of hydrochloric acid (d=1.18) has been added. After cooling at $-10°$ C. for a few hours, the 3-$\beta$-aminoethylamino-4-nitrophenol hydrochloride crystallises. It is filtered off and washed with an ice-cold 2N solution of hydrochloric acid and then with ethanol. After recrystallisation from water, the dried product melts with decomposition at a temperature above 260° C.

| Analysis | Calculated for $C_8H_{12}N_3O_3Cl$ | Found |
|---|---|---|
| C % | 41.11 | 41.22 |
| H % | 5.14 | 5.11 |
| N % | 17.99 | 17.92 |
| O % | 20.55 | 20.44 |
| Cl % | 15.20 | 15.38 |

PREPARATION EXAMPLE 5

Preparation of 2-$\beta$-[N,N-di-($\beta'$-hydroxyethyl)-amino[-ethylamino -5-nitroanisole hydrochloride.

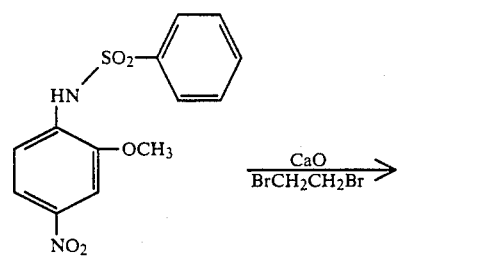

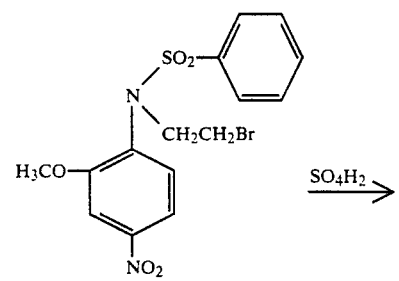

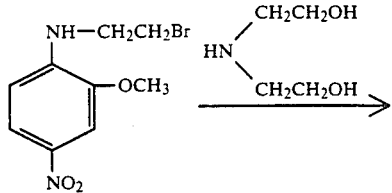

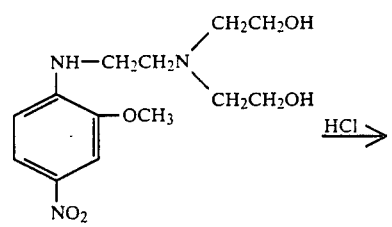

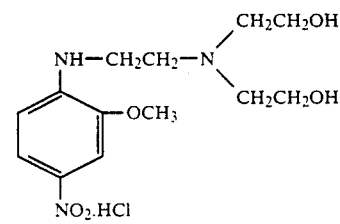

1st step: Preparation of 2-[N-benzenesulphonyl-N-($\beta$-bromoethyl)-amino]-5-nitroanisole.

This compound is obtained by reacting 1,2-dibromoethane with the calcium salt of 2-N-benzenesulphonyl-amino-5-nitroanisole in dimethylformamide at about 80° C., in accordance with the process described in French Patent 1,491,617. This product melts at 122° C.

2nd step: Preparation of 2-N-bromoethylamino-5-nitroanisole.

169 g (0.407 mol) of the substituted benzenesulphonamide obtained in accordance with the previous step are added gradually to 500 ml of 96% strength sulphuric acid, with stirring and whilst keeping the temperature between 15 and 20° C. The reaction medium is kept at this temperature for 1 hour and then poured onto 3 kg of crushed ice. The crystalline product which precipitates is filtered off, washed with water and dried in vacuo at 60° C. It melts at 118° C.

3rd step: Preparation of 2$\beta$-[N,N-di-('-hydroxyethyl)amino]-ethylamino-5-nitroanisole hydrochloride.

41.3 g (0.15 mol) of 2-N-( -bromoethyl)-amino-5-nitroanisole are added gradually, in the course of 25 minutes and with stirring, to 110.4 g (1.05 mols) of diethanolamine heated to about 100° C. beforehand. After heating at about 100° C. for 1½ hours, the reaction medium is poured into 400 g of an ice-cold normal solution of sodium hydroxide and the expected product is extracted with ethyl acetate. The ethyl acetate is driven off in vacuo. The residual red oil is dissolved in 120 ml of absolute alcohol. After the addition of 50 ml of absolute ethanol saturated with hydrogen chloride, a precipitate of 2-$\beta$-[N,N-di-($\beta'$-hydroxyethyl)-amino]-ethylamino-5-nitroanisole hydrochloride is obtained, which, after recrystallisation from 90° strength alcohol and drying in vacuo at 60° C. over potassium hydroxide, melts with decomposition at between 168° and 170° C.

| Analysis | Calculated for $C_{13}H_{21}N_3O_5 \cdot HCl$ | Found |
|---|---|---|
| C % | 46.50 | 46.74 |
| H % | 6.60 | 6.62 |
| N % | 12.51 | 12.51 |
| O % | 23.82 | 23.65 |
| Cl % | 10.56 | 10.36 |

PREPARATION EXAMPLE 6

Preparation of 2-γ-(N,N-dimethylamino)-propylamino-5-nitroanisole hydrochloride.

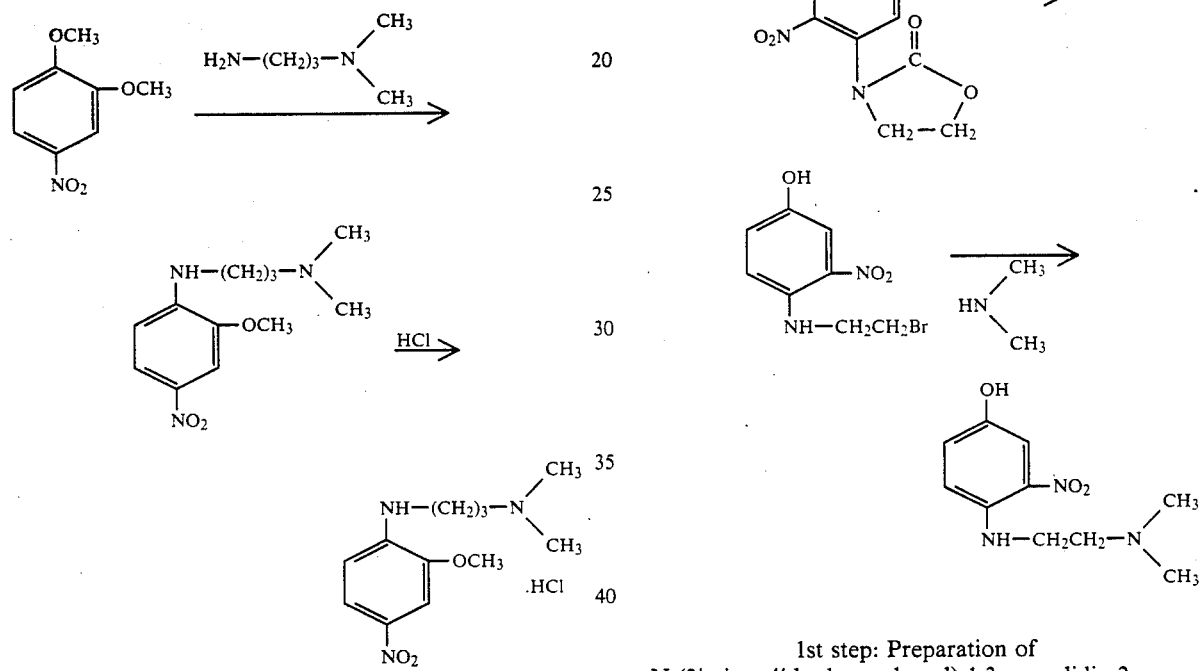

0.4 mol (73.2 g) of 3,4-dimethoxynitrobenzene is introduced into 220 ml of N,N-dimethylpropylenediamine and the solution is heated at 115° C. for 12 hours. The cooled mixture is then poured into 2.200 kg of iced water. The expected product, as the free base, precipitates in the form of an oil, which is extracted with ethyl acetate. The ethyl acetate is driven off in vacuo. The residual red oil is dissolved in 100 ml of absolute ethanol. After the addition of 100 ml of absolute ethanol saturated with hydrogen chloride, a precipitate of 2-γ-(N,N-dimethylamino)-propylamino-5-nitroanisole hydrochloride is obtained, which, after recrystallisation from absolute ethanol and drying in vacuo at 80° C., melts with decomposition at 181° C.

| Analysis | Calculated for $C_{12}H_{20}N_3O_3Cl$ | Found |
|---|---|---|
| C % | 49.74 | 49.74 |
| H % | 6.91 | 6.96 |
| N % | 14.51 | 14.52 |
| O % | 16.58 | 16.48 |
| Cl % | 12.26 | 12.30 |

PREPARATION EXAMPLE 7

Preparation of 3-nitro-4-(N,N-dimethylamino)ethylaminophenol.

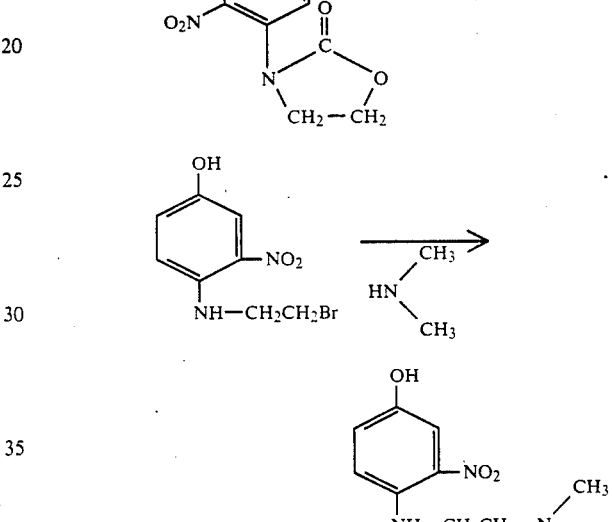

1st step: Preparation of N-(2'-nitro-4'-hydroxyphenyl)-1,3-oxazolidin-2-one.

0.02 mol (5.2 g) of β-chloroethyl N-(2'-nitro-4'-hydroxyphenyl)-carbamate (obtained in accordance with the operation described in Example No. 1 of French Patent 2,348,911) is introduced, with stirring, into 17 ml of a 2.36N solution of sodium hydroxide at 20° C. When the addition has ended, the reaction medium is kept at 20° C. for 30 minutes and then diluted with 20 ml of water and neutralised at 0° C. with a hydrochloric acid solution. The expected product precipitates. It is filtered off, washed with water and recrystallised from ethanol. It melts at 170° C.

| Analysis | Calculated for $C_9H_8N_2O_5$ | Found |
|---|---|---|
| C % | 48.21 | 48.36 |
| H % | 3.57 | 3.59 |
| N % | 12.50 | 12.63 |
| O % | 35.71 | 35.59 |

2nd step: Preparation of 3-nitro-4-(β-bromoethyl)-aminophenol.

0.55 mol (125 g) of N-(2'-nitro-4'-hydroxyphenyl)-1,3-oxazolidin-2-one is added in the course of 10 minutes, with stirring, to 375 ml of 48% strength hydrochloric acid heated to 90° C. beforehand. The reaction medium is kept at 90° C. for 30 minutes and then filtered hot. On cooling of the filtrate, the expected product precipitates in the form of the hydrobromide. The hydrobromide is filtered off and taken up in 500 ml of water, with stirring, in order to free the 3-nitro-4-(β-bromoethyl)-aminophenol, which is filtered off, washed with water and dried in vacuo. After recrystallisation from benzene, the product melts at 122° C.

| Analysis | Calculated for C$_8$H$_9$N$_2$O$_3$Br | Found |
|---|---|---|
| C % | 36.78 | 36.95 |
| H % | 3.45 | 3.49 |
| N % | 10.73 | 10.80 |
| O % | 18.39 | 18.24 |
| Br % | 30.65 | 30.54 |

3rd step: Preparation of
3-nitro-4-(N,N-dimethylamino)-ethylaminophenol.

0.0766 mol (20 g) of 3-nitro-4-(β-bromoethyl)-aminophenol is heated for 20 minutes, at 60° C., in 60 ml of a 40% strength aqueous solution of dimethylamine. The reaction medium is poured into 300 ml of iced water and then neutralised with acetic acid. The expected product precipitates. It is filtered off, washed with water and recrystallised from ethanol. After drying in vacuo, it melts at 151° C.

| Analysis | Calculated for C$_{10}$H$_{15}$N$_3$O$_3$ | Found |
|---|---|---|
| C % | 53.33 | 53.48 |
| H % | 6.67 | 6.77 |
| N % | 18.67 | 18.48 |
| O % | 21.33 | 21.34 |

PREPARATION EXAMPLE 8

Preparation of 3-nitro-4-[N,N-di-(β-hydroxyethyl)-amino]-ethylaminophenol.

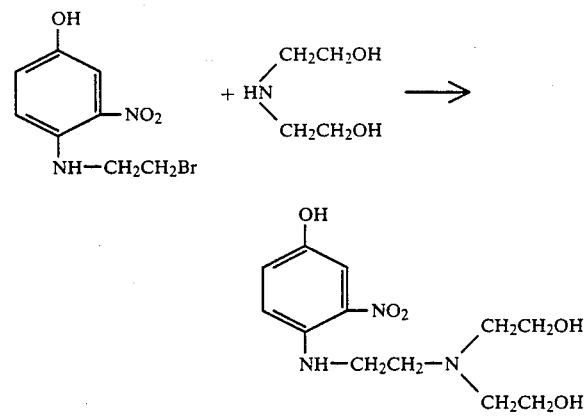

5.2 g (0.02 mol) of 3-nitro-4-(β-bromoethyl)-aminophenol are heated for 1 hour, at 60° C., in 20 ml of diethanolamine. The reaction medium is poured into 100 g of iced water and the solution is then neutralised with acetic acid. After one night at 0° C., the expected product, which has precipitated, is filtered off. After washing with a small amount of iced water and drying in vacuo, the product is recrystallised from ethyl acetate. It melts at 115° C.

| Analysis | Calculated for C$_{12}$H$_{19}$N$_3$O$_5$ | Found |
|---|---|---|
| C % | 50.52 | 50.66 |
| H % | 6.67 | 6.74 |
| N % | 14.74 | 14.58 |
| O % | 28.07 | 28.10 |

PREPARATION EXAMPLE 9

Preparation of 3-β-(N,N-diethylamino)-ethylamino-4-nitro-6-methylanisole.

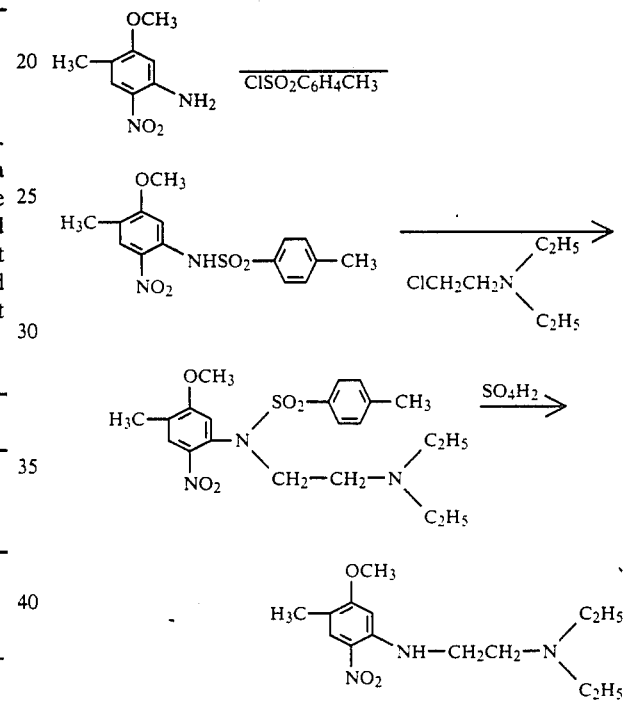

1st step: Preparation of
N-(p-toluenesulphonyl)-amino-4-nitro-6methylanisole.

0.096 mol (18.3 g) of para-toluenesulphonyl chloride is added gradually, with stirring, at between 50° and 55° C., to a solution of 0.058 mol (10.6 g) of 3-amino-4-nitro-6-methylanisole in 60 ml of pyridine. After heating for 3 hours at between 50 and 55° C., the reaction medium is poured into 300 ml of iced water. The expected product, which precipitates, is filtered off, washed with water and recrystallised from dimethylformamide. It melts at 211° C.

| Analysis | Calculated for C$_{15}$H$_{16}$N$_2$O$_5$S | Found |
|---|---|---|
| C % | 53.57 | 53.80 |
| H % | 4.80 | 4.91 |
| N % | 8.33 | 8.45 |
| O % | 23.79 | 23.84 |
| S % | 9.51 | 9.41 |

2nd step: Preparation of 3-[N-(p-toluenesulphonyl)-N-(β-diethylaminoethyl)-amino]-4-nitro-6-methylanisole.

0.0353 mol (11.9 g) of 3-N-(p-toluenesulphonyl)-amino-4-nitro-6-methylanisole is heated, in a boiling water-bath, with stirring, in 50 ml of dimethylformamide to which 2.8 g of quicklime have been added. 0.075 mol (10.2 g) of 2-N,N-diethylamino-1-chloroethane is added gradually. After heating for 3 hours, the reaction mixture is poured into 200 ml of iced water. The expected product crystallises slowly. It is filtered off and washed with water. After drying, it is recrystallised from ethanol. It melts at 114° C.

| Analysis | Calculated for $C_{21}H_{29}N_3O_5S$ | Found |
|---|---|---|
| C % | 57.92 | 57.83 |
| H % | 6.71 | 6.72 |
| N % | 9.65 | 9.68 |
| O % | 18.37 | 18.28 |
| S % | 7.35 | 7.29 |

3rd step: Preparation of 3-β-(N,N-diethylamino)-ethylamino-4-nitro-6-methylanisole.

0.021 mol (9.3 g) of the substituted para-toluenesulphonamide obtained in accordance with the previous step is added gradually to 25 ml of 96% strength sulphuric acid, with stirring and whilst keeping the temperature at between 7° and 10° C. When the addition has ended, the stirring is maintained for 5 hours at ambient temperature and the reaction medium is then poured into 200 ml of iced water.

The reaction medium is rendered alkaline with a 10N solution of sodium hydroxide, with cooling; the expected product precipitates in the form of an oil, which crystallises rapidly. The product is filtered off, washed with water, dried and recrystallised from hexane. It melts at 70° C.

| Analysis | Calculated for $C_{14}H_{23}N_3O_3$ | Found |
|---|---|---|
| C % | 59.76 | 59.64 |
| H % | 8.24 | 8.32 |
| N % | 14.94 | 14.75 |
| O % | 17.06 | 17.21 |

PREPARATION EXAMPLE 10

Preparation of 2-(β-hydroxy-γ-amino)-propylamino-5-nitroanisole hydrochloride.

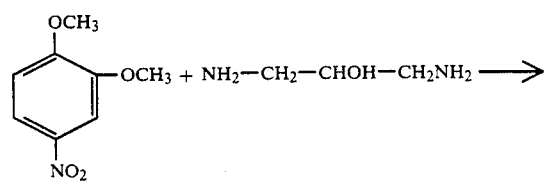

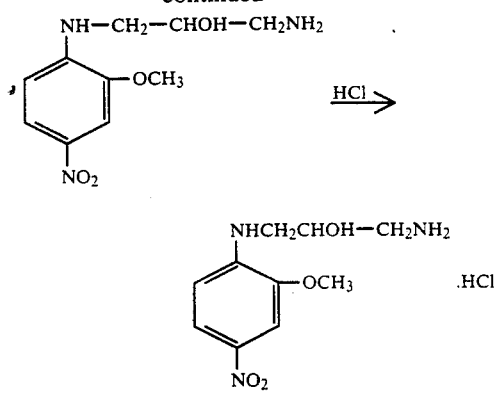

0.0164 mol (3 g) of 3,4-dimethoxynitrobenzene is introduced into 0.177 mol (16 g) of 1,3-diaminopropan-2-ol and the mixture is heated for 4 hours at 100°-110° C. After cooling, the reaction medium is poured into 90 ml of water and the expected product, which has precipitated as the free base, is then filtered off and washed with water. This product is introduced into 40 ml of a 2N solution of hydrochloric acid. After stirring for 30 minutes, the 2(β-hydroxy-γ-amino)-propylamino-5-nitroanisole hydrochloride is filtered off and washed with alcohol. After recrystallisation from water, it melts at 227° C.

| Analysis | Calculated for $C_{10}H_{15}O_4N_3 \cdot HCl$ | Found |
|---|---|---|
| C % | 43.24 | 43.28 |
| H % | 5.70 | 5.82 |
| N % | 15.13 | 15.16 |
| Cl % | 12.79 | 13.04 |

PREPARATION EXAMPLE 11

Preparation of 3-(β-hydroxy-γ-amino)-propylamino-4-nitroanisole.

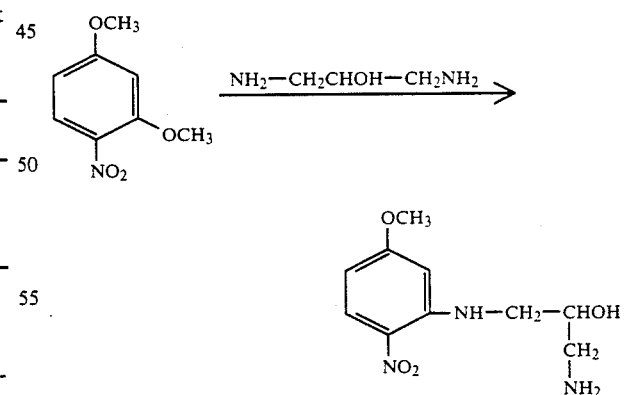

0.0218 mol (4 g) of 2,4-dimethoxynitrobenzene is introduced into 0.177 mol (16 g) of 1,3-diaminopropan-2-ol and the mixture is heated for 3 hours at between 100° and 110° C. After cooling, the reaction medium is poured into 60 ml of water. The expected product precipitates. It is filtered off, washed with water and treated with 40 ml of a 2N solution of hydrochloric acid, with stirring. The 3-(β-hydroxy-γ-amino)- propylamino-4-nitroanisole hydrochloride is filtered off and washed with absolute alcohol.

3 g of the abovementioned hydrochloride are dissolved in 90 ml of boiling water. The solution is filtered hot to remove a small amount of insoluble material, and the filtrate is then rendered alkaline with concentrated ammonia solution. The 3-(β-hydroxy-γ-amino)-propylamino-4-nitroanisole which has precipitated is filtered off, washed with water and dried in vacuo. It melts at 178° C.

| Analysis | Calculated for $C_{10}H_{15}O_4N_3$ | Found |
|---|---|---|
| C % | 49.79 | 49.71 |
| H % | 6.22 | 6.29 |
| N % | 17.43 | 17.24 |

EXAMPLE 1

The following dyeing composition is prepared:

| | |
|---|---|
| 3-α-Dimethylaminopropylamino-4-nitroanisole hydrochloride | 2 g |
| 3-Nitro-4-amino-6-chloro-N-(β-aminoethyl)-aniline hydrochloride | 0.6 g |
| 3-Nitro-4-N'-methylamino-N-(β-aminoethyl)-aniline dihydrobromide | 0.515 g |
| Cellosize WP 03 | 2 g |
| Cetyldimethylhydroxyethylammonium chloride | 2 g |
| 22° B Strength ammonium solution | 2.5 g |
| Water q.s. | 100 g |
| pH 8.5 | |

When applied to naturally light chestnut hair for 25 minutes at 30° C., this mixture imparts to the hair, after rinsing and shampooing, a deep chestnut colouration with a coppery sheen.

EXAMPLE 2

The following dyeing composition is prepared:

| | |
|---|---|
| 2-N-(α-dimethylaminopropyl)-amino-5-nitroanisole hydrochloride | 0.6 g |
| 3-Nitro-4-N-(β-hydroxyethyl)-aminophenol | 0.25 g |
| 3-Nitro-4-amino-N-(-hydroxyethyl)-aniline | 0.26 g |
| 2-N-(β-hydroxyethyl)-amino-5-[4-N,N-di-(β-hydroxyethyl)-amino]-anilino-1,4-benzoquinone | 0.3 g |
| 2-Butoxyethanol | 10 g |
| Cemulsol NP4 | 12 g |
| Cemulsol NP9 | 15 g |
| Oxyethyleneated oleyl alcohol containing 2 mols of ethylene oxide | 1.5 g |
| Oxyethyleneated oleyl alcohol containing 4 mols of ethylene oxide | 1.5 g |
| 20% Strength aqueous solution of triethanolamine | 1 g |
| Water q.s. | 100 g |
| pH 8.7. | |

When applied to 90% naturally white hair for 30 minutes at 30° C., this mixture imparts to the hair, after rinsing and shampooing, a light red colouration.

EXAMPLE 3

The following composition is prepared

| | |
|---|---|
| 3-N-(β-aminoethyl)-amino-4-nitroanisole hydrochloride | 0.4 g |
| 3-Nitro-4-N-(β-hydroxyethyl)-aminophenoxy-ethanol | 0.5 g |
| 3-Nitro-4-N'-methylamino-N-(β-aminoethyl)-aniline dihydrobromide | 0.63 g |
| 2-Butoxyethanol | 6 g |
| Lauramide | 1.5 g |
| Lauric acid | 1 g |
| Hydroxyethylcellulose | 5 g |
| Monoethanolamine | 2 g |
| Water q.s. | 100 g |
| pH 10. | |

When applied for 20 minutes at 25° C. to hair which has been bleached white, this mixture imparts to the hair, after rinsing and shampooing, a coppery-red chestnut colouration.

EXAMPLE 4

The following dyeing composition is prepared:

| | |
|---|---|
| 3-N-(β-aminoethyl)-amino-4-nitroanisole hydrochloride | 0.40 g |
| 3-Nitro-4-(β-hydroxyethyl)-aminophenyl β-hydroxypropyl ether | 0.935 g |
| 3-Nitro-4-N'-(β-aminoethyl)-amino-N,N-di-(-β-hydroxyethyl)-aniline dihydrochloride | 0.605 g |
| 3-Nitro-4-N-(β-hydroxyethyl)-amino-6-chloroaniline | 0.525 g |
| 2-Butoxyethanol | 10 g |
| Alfol C$_{16/18}$ | 8 g |
| Lanette wax E | 0.5 g |
| Cemulsol B | 1 g |
| Oleic diethanolamide | 1.5 g |
| 20% Strength by weight aqueous solution of triethanolamine | 1 g |
| Water q.s. | 100 g |
| pH 7. | |

When applied to 90% naturally white hair for 30 minutes at 28° C., this mixture imparts to the hair, after rinsing and shampooing, a copper-red chestnut shade.

EXAMPLE 5

The following dyeing composition is prepared:

| | |
|---|---|
| 3-β-Diethylaminoethylamino-4-nitroanisole hydrochloride | 0.26 g |
| Tetraaminoanthraquinone | 0.3 g |
| 3-Nitro-4-amino-6-methyl-N-(β-hydroxyethyl)-aniline | 0.15 g |
| Propylene glycol | 10 g |
| Carbopol 934 | 2 g |
| 22° B strength ammonia solution | 4 g |
| Water q.s. | 100 g |
| pH 5.8. | |

When applied for 30 minutes at 28° C. to hair which has been bleached white, this mixture imparts to the hair, after rinsing and shampooing, a golden blond colouration.

EXAMPLE 6

The following dyeing composition is prepared:

| | |
|---|---|
| 3-N-(β-aminoethyl)-amino-4-nitroanisole hydrochloride | 0.8 g |
| 3-N-methylamino-4-nitrophenoxyethanol | 0.11 g |
| 3-Nitro-4-amino-N-(β-hydroxyethyl)-aniline | 0.51 g |
| Tetraaminoanthraquinone | 0.1 g |
| 2-Butoxyethanol | 10 g |
| Cellosize WP 03 | 2 g |
| Cetyldimethylhydroxyethylammonium chloride | 2 g |
| 20% Strength aqueous solution of triethanolamine | 1 g |

-continued

| | |
|---|---|
| Water q.s. | 100 g |
| pH 7.2. | |

When applied to 90% naturally white hair for 25 minutes at 28° C., this mixture imparts to the hair, after rinsing and shampooing, a medium chestnut colouration with a golden sheen.

EXAMPLE 7

The following dyeing composition is prepared:

| | |
|---|---|
| 3-N-(β-aminoethyl)-amino-4-nitroanisole hydrochloride | 1.2 g |
| N,N'-di-(β-hydroxyethyl)-4-nitro-ortho-phenylenediamine | 0.8 g |
| 3-Nitro-4-N'-methylamino-N-(β-aminoethyl)-aniline dihydrobromide | 0.5 g |
| 96° Strength ethanol | 10 g |
| Alfol C$_{16/18}$ | 8 g |
| Lanette wax E | 0.5 g |
| Cemulsol B | 1 g |
| Oleic diethanolamide | 1.5 g |
| 20% Strength aqueous solution of triethanolamine | 2 g |
| Water q.s. | 100 g |
| pH 9.5 | |

When applied for 20 minutes at 28° C. to hair which has been bleached straw yellow, this solution imparts to the hair, after rinsing and shampooing, a coppery chestnut colouration.

EXAMPLE 8

The following dyeing composition is prepared:

| | |
|---|---|
| 2-β-(N,N-diethylamino)-ethylamino-5-nitroanisole hydrochloride | 1.1 g |
| 3-Nitro-4-amino-6-chloro-N-(β-aminoethyl)-aniline hydrochloride | 0.5 g |
| Tetraaminoanthraquinone | 0.5 g |
| 96° Strength ethanol | 10 g |
| Lauramide | 1.5 g |
| Lauric acid | 1 g |
| Hydroxyethylcellulose | 5 g |
| Monoethanolamine | 2 g |
| Water q.s. | 100 g |
| pH 10. | |

When applied to 90% naturally white hair for 25 minutes at 30° C., this mixture imparts to the hair, after rinsing and shampooing, a light chestnut colouration with a coppery sheen.

EXAMPLE 9

The following dyeing composition is prepared:

| | |
|---|---|
| 3-δ-Dimethylaminopropylamino-4-nitroanisole hydrochloride | 0.05 g |
| 3-Nitro-4-amino-6-methylphenol | 0.055 g |
| 3-Nitro-4-N'-methylamino-N,N-di-(β-hydroxyethyl)-aniline | 0.1 g |
| 2-Butoxyethanol | 6 g |
| Lauramide | 1.5 g |
| Lauric acid | 1 g |
| Hydroxyethylcellulose | 5 g |
| Monoethanolamine | 2 g |
| Water q.s. | 100 g |
| pH 10 | |

When applied to bleached hair for 30 minutes at 28° C., this mixture imparts to the hair, after rinsing and shampooing, a golden blond colouration.

EXAMPLE 10

The following dyeing composition is prepared:

| | |
|---|---|
| 3-N-(β-aminoethyl)-amino-4-nitrophenol hydrochloride | 0.4 g |
| 3-Nitro-4-N'-(β-aminoethyl)-amino-N,N-di-(β-hydroxyethyl)-aniline dihydrochloride | 0.2 g |
| 3-Nitro-4-N-(β-hydroxyethyl)-aminophenol | 0.09 g |
| Propylene glycol | 10 g |
| Carboxymethylcellulose | 2 g |
| Ammonium lauryl-sulphate | 5 g |
| 20% Strength aqueous solution of triethanolamine | 1.2 g |
| Water q.s. | 100 g |
| pH 6.5 | |

When applied to 90% naturally white hair for 25 minutes at 30° C., this mixture imparts to the hair, after rinsing and shampooing, a light copper colouration.

EXAMPLE 11

The following dyeing composition is prepared:

| | |
|---|---|
| 3-Nitro-6-N-(β-aminoethyl)-aminoanisole hydrochloride | 0.25 g |
| 3-Nitro-4-N'-methylamino-N-(β-aminoethyl)-aniline dihydrobromide | 0.23 g |
| 3-Nitro-4-amino-6-methyl-N-(β-hydroxyethyl)-aniline | 0.15 g |
| Alfol C$_{16/18}$ | 8 g |
| Lanette wax E | 0.5 g |
| Cemulsol B | 1 g |
| Oleic ethanolamide | 1.5 g |
| 20% Strength aqueous solution of triethanolamine | 1 g |
| Water q.s. | 100 g |
| pH 7.3 | |

When applied to 90% naturally white hair for 25 minutes at 30° C., this mixture imparts to the hair, a light chestnut colouration with a copper-red sheen.

EXAMPLE 12

The following dyeing composition is prepared:

| | |
|---|---|
| 3-Nitro-6-N-[β-(di-β'-hydroxyethylamino)-ethyl]-aminoanisole hydrochloride | 0.16 g |
| 3-Nitro-4-N'-methylamino-N,N-di-(β-hydroxyethyl)-aniline | 0.2 g |
| 3-Nitro-4-N-(β-hydroxyethyl)-aminophenol | 0.1 g |
| 96° Ethanol | 10 g |
| Diethanolamides of copra fatty acids | 2.2 g |
| Lauric acid | 0.8 g |
| Ethylene glycol monoethyl ether | 2 g |
| Monoethanolamine | 1 g |
| Water q.s. | 100 g |
| pH 7.6 | |

When applied for 25 minutes at 28° C. to hair which has been bleached white, this mixture imparts to the hair, after rinsing and shampooing, a copper-red chestnut colouration.

EXAMPLE 13

The following dyeing composition is prepared:

| | |
|---|---|
| 3-N-(β-aminoethyl)-amino-4-nitroanisole hydrochloride | 0.7 g |
| 3-Nitro-4-amino-6-methyl-N-(β-hydroxyethyl)- | 0.233 g |

| -continued | |
|---|---|
| aniline | |
| 3-Nitro-4-amino-N-(β-hydroxyethyl)-aniline | 0.97 g |
| 2-Nitro-N-(β-aminoethyl)-aniline hydrochloride | 0.5 g |
| Cemulsol NP4 | 12 g |
| Cemulsol NP9 | 15 g |
| Oxyethyleneated oleyl alcohol containing 2 mols of ethylene oxide | 1.5 g |
| Oxyethyleneated oleyl alcohol containing 4 mols of ethylene oxide | 1.5 g |
| 20% Strength aqueous solution of triethanolamine | 1 g |
| Water q.s. | 100 g |
| pH 7.5 | |

When applied for 25 minutes at 30° C. to hair which has been bleached straw yellow, this mixtures imparts to the hair, after rinsing and shampooing, an intense red colouration.

EXAMPLE 14

The following dyeing composition is prepared:

| | |
|---|---|
| Para-phenylenediamine | 0.15 g |
| Resorcinol | 0.08 g |
| Meta-aminophenol | 0.04 g |
| Ortho-aminophenol | 0.030 g |
| 2,4-Diaminophenoxyethanol dihydrochloride | 0.042 g |
| 3-Nitro-4-amino-6-methyl-N-(β-hydroxyethyl)-aniline | 0.11 g |
| 3-N-(β-aminoethyl)-amino-4-nitroanisole hydrochloride | 0.6 g |
| Carbopol 934 | 1.5 g |
| 96° Strength ethanol | 11 g |
| 2-Butoxyethanol | 5 g |
| Trimethylcetylammonium bromide | 1 g |
| Trilon B | 0.1 g |
| Thioglycolic acid | 0.2 g |
| 22° B strength ammonia solution | 10 g |
| Water q.s. | 100 g |
| pH 10 | |

100 g of hydrogen peroxide of 20 volumes strength are added at the time of use. When applied to 90% naturally white hair for 30 minutes at 28° C., this mixture imparts to the hair, after rinsing and shampooing, a deep chestnut colouration with a golden sheen.

EXAMPLE 15

The following dyeing composition is prepared:

| | |
|---|---|
| 3-Nitro-4-N,N-dimethylaminoethylaminophenol | 0.7 g |
| Alfol C$_{16/18}$ | 8 g |
| Lanette wax E | 0.5 g |
| Cemulsol B | 1 g |
| Oleic diethanolamide | 1.5 g |
| 20% Strength aqueous solution of monoethanolamine | 1 g |
| Water q.s. | 100 g |
| pH 9. | |

When applied for 25 minutes at 28° C. to hair which has been bleached white, this dyeing solution imparts to the hair, after rinsing and shampooing, a mandarin colouration.

EXAMPLE 16

The following dyeing composition is prepared:

| | |
|---|---|
| 3-Nitro-4-N,N-dimethylaminoethylaminophenol | 0.7 g |
| 3-Nitro-4-N'-(β-aminoethyl)-amino-N,N-di-(β-hydroxyethyl)-aniline dihydrochloride | 0.605 g |
| 3-N-(β-aminoethyl)-amino-4-nitroanisole hydrochloride | 0.4 g |
| 96° Strength ethanol | 5 g |
| Alfol C$_{16/18}$ | 8 g |
| Lanette wax E | 0.5 g |
| Cemulsol B | 1 g |
| Oleic diethanolamide | 1.5 g |
| 20% Strength aqueous solution of monoethanolamine | 1 g |
| Water q.s. | 100 g |
| pH 8.3. | |

When applied to 90% naturally white hair for 30 minutes at 30° C., this mixture imparts to the hair, after rinsing and shampooing, a copper-red light chestnut colouration.

The Examples which follow are intended to illustrate other compositions according to the invention. Each example mentions the shades, according to the Munsell scale, on bleached hair or 90% naturally white hair, after application of the compositions to the hair under the conditions given above.

EXAMPLE 17

| | |
|---|---|
| 3-N-(β-aminoethyl)-amino-4-nitroanisole hydrochloride | 0.1 g |
| 2-Butoxyethanol | 10 g |
| Nonylphenol containing 4 mols of ethylene oxide | 12 g |
| Nonylphenol containing 9 mols of ethylene oxide | 15 g |
| Oxyethyleneated oleyl alcohol containing 2 mols of ethylene oxide | 1.5 g |
| Oxyethyleneated oleyl alcohol containing 4 mols of ethylene oxide | 1.5 g |
| 20% Strength aqueous solution of monoethanolamine | 1 g |
| Water q.s. | 100 g |
| pH 10. | |

On bleached hair: 5.5 Y 8/6.
On 90% naturally white hair: 5.5 Y 6/4.

EXAMPLE 18

| | |
|---|---|
| 3-N-(β-aminoethyl)-amino-4-nitrophenol hydrochloride | 0.2 g |
| 2-Butoxyethanol | 10 g |
| Diethanolamides of copra fatty acids | 2.2 g |
| Lauric acid | 0.8 g |
| Ethylene glycol monoethyl ether | 2 g |
| Monoethanolamine | 1 g |
| Water q.s. | 100 g |
| ph 6.8 | |

On bleached hair: 6.5 Y 8.5/8.
On 90% naturally white hair: 6.5 Y 6.5/6.

EXAMPLE 19

| | |
|---|---|
| 3-β-Diethylaminoethylamino-4-nitroanisole hydrochloride | 1 g |
| 96° Strength ethanol | 10 g |
| Alfol C$_{16/18}$ | 8 g |
| Lanette wax E | 0.5 g |
| Cemulsol B | 1 g |
| Oleic diethanolamide | 1.5 g |
| 20% Strength aqueous solution of monoethanolamine | 0.5 g |
| Water q.s. | 100 g |
| pH 7.7. | |

On bleached hair: 7 Y 8/9.
On 90% naturally white hair: 7 Y 6.5/6.

EXAMPLE 20

| | |
|---|---|
| 3-δ-Dimethylaminopropylamino-4-nitroanisole hydrochloride | 0.4 g |
| 2-Butoxyethanol | 10 g |
| Hydroxyethylcellulose | 2 g |
| Cetyldimethylhydroxyethylammonium chloride | 2 g |
| 20% Strength aqueous solution of triethanolamine | 1 g |
| Water q.s. | 100 g |
| pH 8 | |

On bleached hair: 7 Y 8/10.
On 90% naturally white hair: 7 Y 7/6.

EXAMPLE 21

| | |
|---|---|
| 3-Nitro-6-N-(β-aminoethyl)-aminoanisole hydrochloride | 0.55 g |
| 2-Butoxyethanol | 10 g |
| Carboxymethylcellulose | 2 g |
| Ammonium lauryl-sulphate | 5 g |
| 20% Strength aqueous solution of monoethanolamine | 2 g |
| Water q.s. | 100 g |
| pH 9.5. | |

On bleached hair: 7 Y 8/13.
On 90% naturally white hair: 7 Y 6.5/8.

EXAMPLE 22

| | |
|---|---|
| 3-Nitro-6-N-(β-aminoethyl)-aminoanisole hydrochloride | 0.05 g |
| 2-Butoxyethanol | 6 g |
| Lauramide | 1.5 g |
| Lauric acid | 1 g |
| Hydroxyethylcellulose | 5 g |
| Monoethanolamine | 2 g |
| Water q.s. | 100 g |
| pH 10.4. | |

On bleached hair: 7 Y 8/6.
On 90% naturally white hair: 7 Y 7/4.

EXAMPLE 23

| | |
|---|---|
| 2-N,N-diethylaminoethyl-5-nitroanisole hydrochloride | 0.705 g |
| 2-Butoxyethanol | 10 g |
| Diethanolamides of copra fatty acids | 2.2 g |
| Lauric acid | 0.8 g |
| Ethylene glycol monoethyl ether | 2 g |
| Monoethanolamine | 1 g |
| Water q.s. | 100 g |
| pH 6.6 | |

On bleached hair: 7.5 Y 8/10.
On 90% naturally white hair: 7.5 Y 6/6.

EXAMPLE 24

| | |
|---|---|
| 2-γ-(N,N-dimethylamino)-propylamino-5-nitroanisole hydrochloride | 1 g |
| 96° Strength ethanol | 10 g |
| Cemulsol NP4 | 12 g |
| Cemulsol NP9 | 15 g |
| Oxyethyleneated oleyl alcohol containing 2 mols of ethylene oxide | 1.5 g |
| Oxyethyleneated oleyl alcohol containing 4 mols of ethylene oxide | 1.5 g |
| 20% Strength aqueous solution of triethanolamine | 2 g |
| Water q.s. | 100 g |
| pH 8. | |

On bleached hair: 7.5 Y 8.5/14.
On 90% naturally white hair: 7.5 Y 6/8.

EXAMPLE 25

| | |
|---|---|
| 2-β-[N,N-di-(β'-hydroxyethyl)-amino]-ethylamino-5-nitroanisole hydrochloride | 2 g |
| 2-Butoxyethanol | 10 g |
| Hydroxyethylcellulose | 2 g |
| Cetyldimethylhydroxyethylammonium chloride | 2 g |
| 20% Strength aqueous solution of monoethanolamine | 2.5 g |
| Water q.s. | 100 g |
| pH 9 | |

On bleached hair: 7.5 Y 8/13.
On 90% naturally white hair: 7.5 Y 6/8.

EXAMPLE 26

| | |
|---|---|
| 3-N-(β-aminoethyl)-amino-4-nitroanisole hydrochloride | 0.258 g |
| 3-N,N-diethylaminoethylamino-4-nitroanisole hydrochloride | 0.305 g |
| 2-Methylresorcinol | 0.20 g |
| Meta-aminophenol | 0.08 g |
| 2,4-Diaminophenyl β-hydroxypropyl ether dihydrochloride | 0.09 g |
| Para-phenylenediamine | 0.105 g |
| Oxyethyleneated nonylphenol containing 4 mols of ethylene oxide | 12 g |
| Oxyethyleneated nonylphenol containing 9 mols of ethylene oxide | 12 g |
| Oleyl alcohol containing 2 mols of ethylene oxide | 1.5 g |
| Oleyl alcohol containing 4 mols of ethylene oxide | 1.5 g |
| Propylene glycol | 6 g |
| Trilon B | 0.12 g |
| 22° B strength ammonia solution | 11 g |
| Thioglycolic acid | 0.6 g |
| Water q.s. | 100 g |
| pH 10 | |

100 g of hydrogen peroxide of 20 volumes strength are added at the time of use.

When applied to 90% naturally white hair for 25 minutes at 30° C., this mixture imparts to the hair, after rinsing and shampooing, a blue-grey colouration with a metallic sheen.

EXAMPLE 27

The following dyeing composition is prepared:

| | |
|---|---|
| 3-Nitro-4-[N,N-di-(β-hydroxyethyl)-amino]-ethylaminophenol | 0.41 g |
| 3-N,N-dimethylaminoethylamino-4-nitroanisole monohydrochloride | 1.34 g |
| 3-Nitro-4-N'-(β-aminoethyl)-amino-N,N-di-(β-hydroxyethyl)-aniline dihydrochloride | 0.26 g |
| 3-Nitro-4-amino-6-methyl-N-(β-hydroxyethyl)-aniline | 0.1 g |
| Cellosize WP03 | 2 g |
| Cetyldimethylhydroxyethylammonium chloride | 2 g |
| 5% Strength ammonia solution | 5 g |
| Water q.s. | 100 g |
| pH 8 | |

When applied to 90% naturally white hair for 15 minutes at 30° C., this mixture imparts to the hair, after rinsing and shampooing, a copper medium chestnut colouration.

EXAMPLE 28

The following dyeing composition is prepared:

| | |
|---|---|
| 3-β-(N,N-diethylamino)-ethylamino-4-nitro-6-methylanisole | 0.15 g |
| 3-Nitro-4-N-(β-hydroxyethyl)-aminophenyl β-hydroxypropyl ether | 0.10 g |
| 3-Nitro-4-N'-(β'-aminoethyl)-amino-N,N-di-(β-hydroxyethyl)-aniline dihydrochloride | 0.135 g |
| 2-Butoxyethanol | 10 g |
| Diethanolamides of copra fatty acids | 2.2 g |
| Lauric acid | 0.8 g |
| Ethylene glycol monoethyl ether | 2 g |
| Monoethanolamine | 1 g |
| Water q.s. | 100 g |
| pH 7 | |

When applied to bleached hair for 30 minutes at 30° C., this mixture imparts to the hair, after rinsing and shampooing, a hazel colouration.

EXAMPLE 29

The following dyeing composition is prepared:

| | |
|---|---|
| 3-β-(N,N-diethylamino)-ethylamino-4-nitro-6-Methylanisole | 0.805 g |
| 2-Butoxyethanol | 10 g |
| Alfol C16/18 | 8 g |
| Lanette wax E | 0.5 g |
| Cemulsol B | 1 g |
| Oleic diethanolamide | 1.5 g |
| 5% Strength ammonia solution | 0.35 g |
| Water q.s. | 100 g |
| pH 8.5. | |

When applied to bleached hair for 20 minutes at 25° C., this mixture imparts to the hair, after rinsing and shampooing, a very intense yellow colouration.

EXAMPLE 30

The following dyeing composition is prepared:

| | |
|---|---|
| 2-(β-Hydroxy-γ-amino)-propylamino-5-nitroanisole hydrochloride | 0.3 g |
| 3-Nitro-4-N-(β-hydroxyethyl)-aminophenol | 0.2 g |
| 3-Nitro-4-N'-methylamino-N,N-di-(β-hydroxyethyl)-aniline | 0.5 g |
| Propylene glycol | 10 g |
| Hydroxyethylcellulose | 2 g |
| Cetyldimethylhydroxyethylammonium chloride | 2 g |
| 20% Strength triethanolamine solution | 1 g |
| Water q.s. | 100 g |
| pH 7.6 | |

When applied to 90% naturally white hair for 30 minutes at 30° C., this mixture imparts to the hair, after rinsing and shampooing, a coppery blond colouration.

EXAMPLE 31

The following dyeing composition is prepared:

| | |
|---|---|
| 2-(β-Hydroxy-γ-amino)-propylamino-5-nitroanisole hydrochloride | 0.2 g |
| Hydroxyethylcellulose | 2 g |
| Ammonium lauryl-sulphate | 5 g |
| 96° Strength ethanol | 10 g |
| Water q.s. | 100 g |
| pH 7.4 | |

When applied to bleached hair for 30 minutes at 28° C., this mixture imparts to the hair, after rinsing and shampooing, a colouration of 5.5 Y 8.5/8 according to the Munsell scale.

EXAMPLE 32

The following dyeing composition is prepared:

| | |
|---|---|
| 3-(β-Hydroxy-γ-amino)-propylamino-4-nitroanisole | 0.36 g |
| 2-Butoxyethanol | 5 g |
| Diethanolamides of copra fatty acids | 2.2 g |
| Lauric acid | 0.8 g |
| Ethylene glycol monoethyl ether | 2 g |
| Monoethanolamine | 0.5 g |
| Water q.s. | 100 g |
| pH 8.9 | |

When applied to bleached hair for 25 minutes at 28° C., this mixture imparts to the hair, after rinsing and shampooing, a colouration of 6.0 Y 8/10 according to the Munsell scale.

EXAMPLE 33

The following dyeing composition is prepared:

| | |
|---|---|
| 3-β-Aminoethylamino-4-nitroanisole hydrochloride | 0.238 g |
| 3-β-Diethylaminoethylamino-4-nitroanisole hydrochloride | 0.305 g |
| 2-Methylresorcinol | 0.2 g |
| Meta-aminophenol | 0.08 g |
| 2,4-Diaminophenyl β-hydroxypropyl ether dihydrochloride | 0.09 g |
| Para-phenylenediamine | 0.105 g |
| Oxyethyleneated nonylphenol containing 4 mols of ethylene oxide | 12 g |
| Oxyethyleneated nonylphenol containing 9 mols of ethylene oxide | 12 g |
| Oleyl alcohol containing 2 mols of ethylene oxide | 1.5 g |
| Oleyl alcohol containing 4 mols of ethylene oxide | 1.5 g |
| Propylene glycol | 6 g |
| Ethylenediaminetetraacetic acid | 0.12 g |
| 22° B strength ammonia solution | 11 g |
| Thioglycolic acid | 0.6 g |
| Water q.s. | 100 g |
| pH 10 | |

100 g of hydrogen peroxide of 20 volumes strength are added at the time of use. When applied to 95% naturally white hair for 20 minutes at 30° C., this mixture imparts to the hair, after rinsing and shampooing, an ashen grey colouration.

EXAMPLE 34

The following dyeing composition is prepared:

| | |
|---|---|
| Paraphenylene diamine | 0.15 g |
| Meta-aminophenol | 0.08 g |
| Ortho-aminophenol | 0.03 g |
| (2-Amino-4-N-β-hydroxyethylamino)phenyl, β-hydroxypropyl ether | 0.04 g |
| 3-Nitro-4-amino-6-methyl-N-β-hydroxyethyl aniline | 0.11 g |
| 3-N-β-Aminoethylamino-4-nitro anisole hydrochloride | 0.6 g |
| Carbopol 934 | 1.5 g |
| 96° Ethanol | 11 g |
| 2-Butoxy ethanol | 5 g |
| Trimethyl cetyl ammonium bromide | 1 g |
| Trilon B | 0.1 g |

-continued

| | |
|---|---|
| Thioglycolic acid | 0.2 g |
| Ammonia 22° B | 10 g |
| Water q s p | 100 g |
| pH 10 | |

At the moment of use an equal weight of 20 volume hydrogen peroxide is added. The mixture is applied for 30 minutes to 90% natural white hair giving it, after rinsing and shampooing, a chestnut brown colour with golden highlights.

The reference Examples which follow are intended to illustrate the preparation of nitro dyestuffs used in the compositions according to the invention, in association with the dyestuffs of the formula (I).

REFERENCE EXAMPLE 1

Preparation of
3-nitro-4-N-(β-hydroxyethyl)-aminophenyl β-hydroxypropyl ether

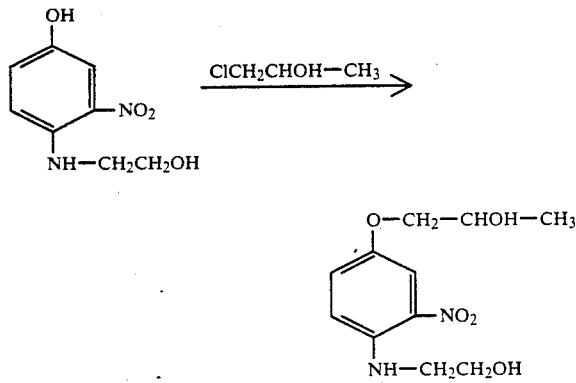

A solution of 0.2 mol (39.6 g) of 3-nitro-4-N-(β-hydroxyethyl)-aminophenol in 104 ml of a 2.3N solution of sodium hydroxide (0.24 mol) is preheated to about 100° C. and 0.24 mol (22.7 g) of 1-chloropropan-2-ol is then added thereto. After the reaction medium has been kept in a boiling water-bath for 2 hours, it is treated with 12 ml of a 10N solution of sodium hydroxide and with 0.12 mol (11.34 g) of 1-chloropropan-2-ol. The heating in the boiling water-bath is maintained for a further 2 hours. After cooling to 0° C., the medium is rendered alkaline to pH 9 with a sodium hydroxide solution. The expected product crystallises and it is filtered off and washed with a normal solution of sodium hydroxide and then with water. After drying in vacuo at 60° C., it melts at 118° C. After recrystallisation once from ethanol and once from ethyl acetate, it melts at 122° C.

| Analysis | Calculated for $C_{11}H_{16}N_2O_5$ | Found |
|---|---|---|
| C% | 51.56 | 51.73 |
| H% | 6.29 | 6.24 |
| N% | 10.93 | 10.82 |
| O% | 31.22 | 31.15 |

REFERENCE EXAMPLE 2

Preparation of
3-nitro-4-(β-aminoethyl)-aminophenoxyethanol

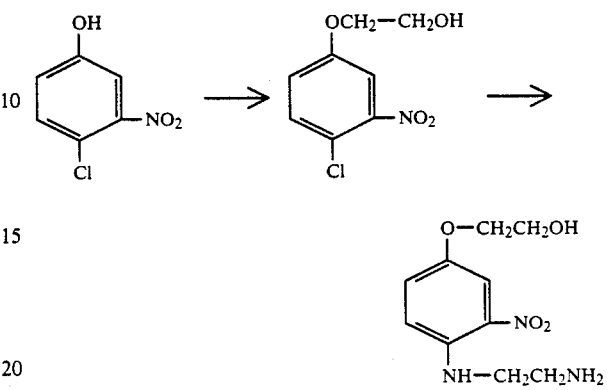

1st step: Preparation of 3-nitro-4-chlorophenoxyethanol 2.5 mols (434 g) of 4-chloro-3-nitrophenol are dissolved in 1,300 ml of dimethylformamide heated to 70° C. beforehand. 3 mols of powdered potassium hydroxide (210 g of 80% pure potassium hydroxide) are added to this solution, and 3 mols (534 g) of glycol bromohydrin are then introduced in the course of 30 minutes, with stirring and whilst keeping the temperature at 70° C. When the addition has ended, the reaction medium is kept at 70° C. for 1 hour. 1 mol of powdered potassium hydroxide (70 g of 80% pure potassium hydroxide) and 1 mol of glycol bromohydrin (178 g) are then added. After heating for 1 hour, a further 1 mol of potassium hydroxide and 1 mol of glycol bromohydrin are added. The heating is continued for a further 1 hour and the cooled reaction medium is then poured into 7.5 liters of iced water. The expected product precipitates. It is filtered off and washed carefully with a 3N solution of sodium hydroxide and then with water. After drying in vacuo, it melts at 96° C.

2nd step: Preparation of
3-nitro-4-(β-aminoethyl)-aminophenoxyethanol 0.4 mol (87 g) of 3-nitro-4-chlorophenoxyethanol is heated under reflux, for 1 hour, in 225 ml of ethylenediamine. The cooled reaction medium is poured into 500 g of iced water. The solution is rendered alkaline to pH 10 with a 10N solution of sodium hydroxide. The expected product crystallises. It is filtered off, washed with cold water and dried in vacuo at 50° C. It melts at 110° C. After recrystallisation from ethanol, it melts at 112° C.

| Analysis | Calculated for $C_{10}H_{15}N_3O_4$ | Found |
|---|---|---|
| C% | 49.78 | 49.86 |
| H% | 6.27 | 6.32 |
| N% | 17.42 | 17.35 |
| O% | 26.53 | 26.41 |

REFERENCE EXAMPLE 3

Preparation of 2,4-diaminophenyl β-hydroxypropyl ether dihydrochloride.

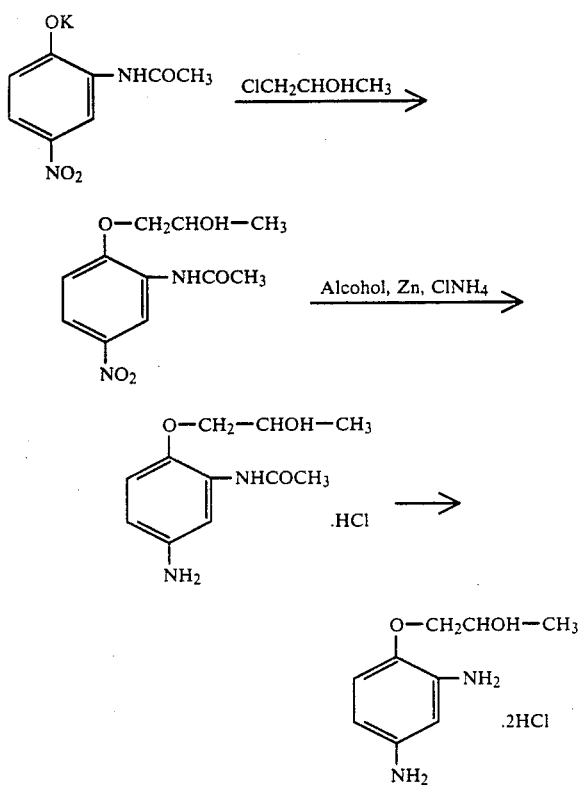

1st step: Preparation of 2-acetylamino-4-nitrophenyl β-hydroxypropyl ether 0.5 mol (117 g) of the potassium salt of 4-nitro-2-acetylaminophenol is introduced into 300 ml of dimethylformamide in a boiling water-bath, with stirring. The mixture is treated with 0.5 mol (47.25 g) of 1-chloropropan-2-ol. With the heating maintained, 0.5 mol (47.25 g) of 1-chloropropan-2-ol and 0.25 mol (34.5 g) of potassium carbonate are added four times at 2-hour intervals. After heating for 10 hours, the reaction mixture is poured into 1,500 ml of iced water. The expected product, which has precipitated, is filtered off. It is washed with a 0.5N solution of sodium hydroxide and then with water. After drying in vacuo at 60° C., it melts at 123° C.

| Analysis | Calculated for $C_{11}H_{14}N_2O_5$ | Found |
|---|---|---|
| C% | 51.96 | 52.18 |
| H% | 5.55 | 5.60 |
| N% | 11.02 | 11.22 |
| O% | 31.47 | 31.44 |

2nd step: 2-Acetylamino-4-aminophenyl β-hydroxypropyl ether monohydrochloride 1.5 g of ammonium chloride and 37.5 g of powdered zinc are added to 70 ml of an aqueous-ethanolic solution (60 ml of $C_2H_5OH$/10 ml of $H_2O$) and this mixture is preheated to the reflux temperature, with stirring. 0.048 mol (12.2 g) of 2-acetylamino-4-nitrophenyl β-hydroxypropyl ether is then added, the addition being adjusted so as to maintain the reflux without heating. When the addition has ended, the mixture is kept under reflux for 10 minutes and filtered at the boil onto a mixture of 5 ml of ethanol and 5.1 ml of 36% strength hydrochloric acid, cooled to −20° C. The expected product precipitates in the form of the monohydrochloride. It is filtered off, washed with a small amount of ice-cold ethanol and dried in vacuo at 50° C. It melts with decomposition at between 220° and 225° C.

| Analysis | Calculated for $C_{11}H_{16}N_2O_3 \cdot HCl$ | Found |
|---|---|---|
| C% | 50.67 | 50.82 |
| H% | 6.57 | 6.61 |
| N% | 10.74 | 10.82 |
| O% | 18.41 | 18.59 |
| Cl% | 13.60 | 13.58 |

3rd step: Preparation of 2,4-diaminophenyl β-hydroxypropyl ether dihydrochloride 0.109 mol (28.4 g) of 2-acetylamino-4-aminophenyl β-hydroxypropyl ether monohydrochloride is dissolved, under reflux, in a mixture of 80 ml of ethanol saturated with hydrogen chloride and 25 ml of 36% strength hydrochloric acid. The reaction mixture is heated under reflux for 1½ hours. On cooling, the expected product precipitates in the form of the dihydrochloride. The product is filtered off, washed with a small amount of absolute alcohol and dried in vacuo at 50° C. It melts with decomposition at between 215° and 220° C.

| Analysis | Calculated for $C_9H_{14}N_2O_2 \cdot 2HCl$ | Found |
|---|---|---|
| C% | 42.36 | 42.27 |
| H% | 6.32 | 6.33 |
| N% | 10.98 | 10.96 |
| O% | 12.54 | 12.55 |
| Cl% | 27.79 | 27.62 |

REFERENCE EXAMPLE 4

Preparation of (2-amino-4-N-β-hydroxyethylamino) phenyl, β-hydroxypropyl ether

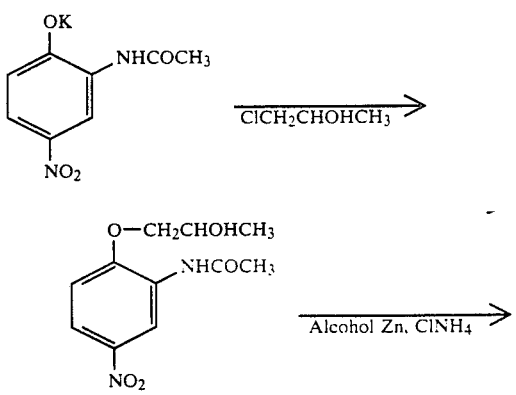

-continued

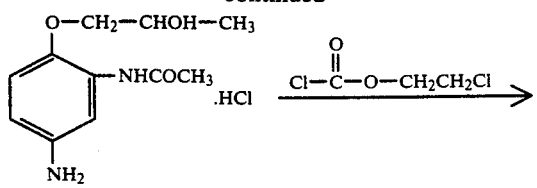

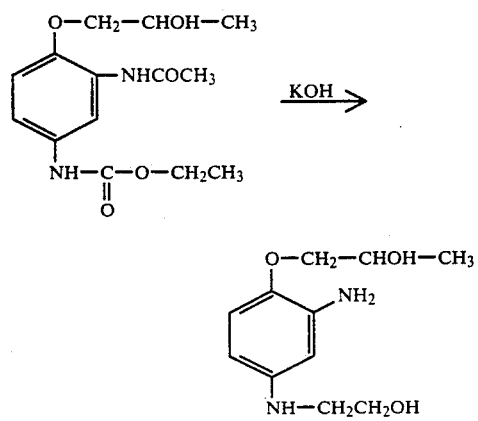

First Step: Preparation of (2-acetylamino-4-nitro) phenyl,β-hydroxypropyl ether 0.5 mol (117 g) of the potassium salt of 4-nitro-2-acetylamino phenol was introduced into 300 ml of dimethyl formamide with agitation on a boiling water bath. 0.5 mol (47.25 g) of 1-chloro-2-propanol is added to the mixture. While maintaining the heat, every two hours, in four portions, 0.5 mol (47.25 g) of 1-chloro-2-propanol and 0.25 mol (35.5 g) of sodium carbonate (each time) is added. After ten hours heating, the reaction mixture is poured into 150 ml of iced water. The expected product which precipitates is dried. It is washed with 0.5N sodium hydroxide solution and then with water. After drying under reduced pressure at 60° C., it melts at 123° C.

| Analysis | Calculated for $C_{11}H_{14}N_2O_5$ | Found |
|---|---|---|
| C% | 51.96 | 52.18 |
| H% | 5.55 | 5.60 |
| N% | 11.02 | 11.22 |
| O% | 31.47 | 31.44 |

Second Step: (2-acetylamino-4-amino)phenyl, β-hydroxy propyl ether monohydrochloride To 70 ml of ethanol solution (60 ml C$_2$H$_5$OH/ 10 ml H$_2$O) are added 1.5 g of ammonium chloride and 37.5 g of powdered zinc and this mixture is brought, with agitation, under reflux. Then 0.048 mole (12.2 g) of (2-acetylamino-4-nitro)phenyl,β-hydroxypropyl ether is added controlling the addition so as to maintain reflux without heating. After the addition is complete, reflux is maintained for 10 minutes and then the mixture is filtered while boiling onto 5 ml cf ethanol to which 5.1 ml of 36% hydrochloric acid has been added, and cooled to −20° C. The expected product precipitates in the form of the monohydrochloride and it is drained, washed with a little iced ethanol and then dried under vacuum at 50° C. It melts with decomposition between 220° and 225° C.

| Analysis | Calculated for $C_{11}H_{16}N_2O_3$,HCl | Found |
|---|---|---|
| C% | 50.67 | 50.82 |
| H% | 6.57 | 6.61 |
| N% | 10.74 | 10.82 |
| O% | 18.41 | 18.59 |
| Cl% | 13.60 | 13.58 |

Third Step: Preparation of β-chloroethyl,N-(3-acetyl amino,β-hydroxypropoxy)phenyl carbamate 0.2 mol (52 g) of (2-acetylamino-4-amino) phenyl,β-hydroxypropyl ether monohydrochloride in 160 ml of dioxane containing 40 ml of 5N sodium hydroxide solution and 11 g of calcium carbonate. The mixture is raised to 90° C. adding, little by little, with stirring, 0.2 mole (28.6 g) of chloroethyl chloroformate. Once the addition is complete, heating is maintained for about 20 minutes and then the reaction mixture is poured into 1 liter of iced water. The expected product precipitates in the form of an oil which crystallises rapidly. The product is drained, washed with water and dried. It melts at 130° C.

Fourth Step: Preparation of (2-amino-4-N-β-hydroxyethyl amino) phenyl,β-hydroxypropyl ether 0.07 mole (23 g) of the compound obtained in the preceding step is introduced into 140 ml of 5N potassium hydroxide solution. The reaction mixture is heated under agitation on a boiling water bath for 1 hour and then cooled. The expected product crystallises, it is drained, washed with water and then with alcohol and then dried under vacuum and recrystallised in ethanol to give the expected product which melts at 123° C.

| Analysis | Calculated for $C_{11}H_{18}N_2O_3$ | Found |
|---|---|---|
| C% | 58.41 | 58.36 |
| H% | 7.96 | 7.99 |
| N% | 12.39 | 12.22 |
| O% | 21.24 | 21.29 |

The tradenames used in the Examples denote the following products:

Cemulsol NP4 Nonylphenol containing 4 mols of ethylene oxide, sold by Rhôone Poulenc.
Cemulsol NP9 Nonylphenol containing 9 mols of ethylene oxide, sold by Rhône Poulenc.
Cellosize WP03 Hydroxyethylcellulose sold by Union Carbide.
Lauramide Lauric acid monoethanolamide sold by Witco.
Alfol C$_{16/18}$ Cetyl/stearyl alcohol sold by Condea.
Lanette wax E Partially sulphated cetyl/ stearyl alcohol sold by Henkel.
Cemulsol B Oxyethyleneated castor oil sold by Rhône-Poulenc.
Carbopol 934 Acrylic acid polymer having a molecular weight of 2 to 3 million, sold by Goodrich Chem. Company.

We claim:

1. A composition suitable for dyeing keratin fibres which comprises, in an acceptable diluent or carrier, at least one dyestuff corresponding to the formula:

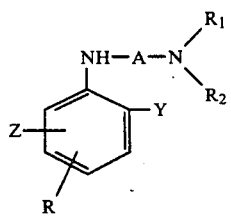 (I)

in which A denotes an alkylene group, an alkylene group substituted by one or more OH groups, or an alkylene group containing a chain hetero-atom group, $R_1$ and $R_2$, which are identical or different, denote hydrogen, alkyl, monohydroxyalkyl or polyhydroxyalkyl, R denotes hydrogen or lower alkyl, and Y denotes alkoxy or $NO_2$, such that if Y denotes alkoxy, Z denotes $NO_2$ and is located in the para-position to the amine group, and if Y denotes $NO_2$, (a) Z denotes alkoxy or OH and is located in the para-position to the $NO_2$ group, or (b) Z denotes OH and is located in the para-position to the amine group, or a cosmetically acceptable salt thereof.

2. A composition according to claim 1 in which the dyestuff corresponds to the formula:

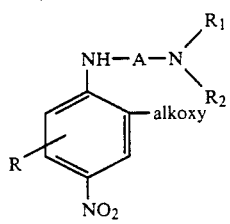 (IA)

in which $R_1$, $R_2$, R and A are as defined in claim 1.

3. A composition according to claim 1 in which the dyestuff corresponds to the formula:

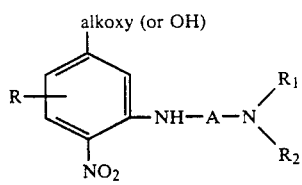 (IB)

in which $R_1$, $R_2$, R and A are as defined in claim 1.

4. A composition according to claim 1 in which the dyestuff corresponds to the formula:

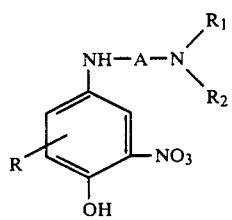 (IC)

in which $R_1$, $R_2$, R and A are as defined in claim 1.

5. A composition according to claim 1 in which the dyestuff corresponds to the formula:

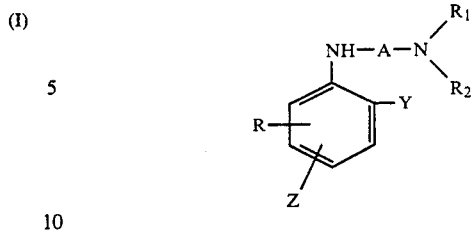

in which $R_1$, $R_2$, Y, R and Z are as defined in claim 1 and A denotes $-CH_2-CHOH-CH_2-$.

6. A composition according to claim 1 which is suitable for dyeing human hair.

7. A composition according to claim 6 which contains, in a cosmetically acceptable medium, at least one compound of formula (I) in an amount of 0.001 to 5% by weight.

8. A composition according to claim 1 which comprises, as solvent, water, a lower alkanol, polyol, glycol or glycol ether, or a mixture thereof.

9. A composition according to claim 6 which also contains at least one cosmetic adjuvant which is a surface-active agent, thickener, penetrating agent, sequestering agent, film-forming agent, buffer, perfume or alkalising or acidifying agent.

10. A composition according to claim 6 intended for use in direct dyeing of the hair, which also contains another direct dyestuff which is an azo, anthraquinone or aminoquinone dyestuff, or a nitrobenzene derivative other than one of formula (I).

11. A composition according to claim 6, intended for use as a setting lotion, which is in the form of an aqueous, alcoholic or aqueous-alcoholic solution containing at least one cosmetic resin.

12. A composition according to claim 10 which has a pH of 3 to 11.5.

13. A composition according to claim 12 which has a pH of 5 to 11.5.

14. A composition according to claim 6 intended for use in oxidation dyeing, which contains at least one oxidation dyestuff precursor.

15. A composition according to claim 14 which has a pH of 7 to 11.5 and also contains a reducing agent and/or antioxidant.

16. A nitroaniline which corresponds to the formula:

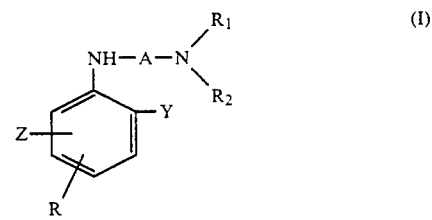 (I)

in which A denotes an alkylene group substituted by one or more OH groups or an alkylene group containing a chain hetero-atom, $R_1$ and $R_2$, which are identical or different, denote hydrogen, alkyl, monohydroxyalkyl or polyhydroxyalkyl, R denotes hydrogen or lower alkyl, and Y denotes an alkoxy or $NO_2$, such that:

if Y denotes alkoxy, then Z denotes $NO_2$ and is located in the para-position with respect to the amine group; and if Y denotes NO$_2$, then either (a) Z denotes alkoxy or OH and is located in the para-position with respect to the NO$_2$ or (b) Z denotes OH and is located in the para-position with respect to the amine group.
17. A nitroaniline according to claim 16 in which A denotes the radical —CH$_2$CHOH—CH$_2$.
18. A nitroaniline according to claim 17 which corresponds to the formula:
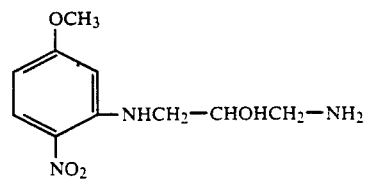
or
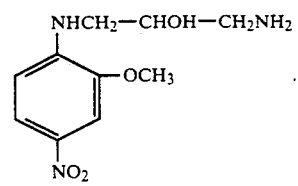
* * * * *